US010401350B2

(12) United States Patent
Nagai et al.

(10) Patent No.: US 10,401,350 B2
(45) Date of Patent: Sep. 3, 2019

(54) SAMPLE ANALYZER AND COMPUTER PROGRAM PRODUCT

(71) Applicant: SYSMEX CORPORATION, Kobe-shi, Hyogo (JP)

(72) Inventors: Takaaki Nagai, Kobe (JP); Noriyuki Narisada, Kobe (JP); Daigo Fukuma, Kobe (JP); Masanori Imazu, Kobe (JP)

(73) Assignees: Sysmex Corporation, Kobe (JP); Sysmex America, Inc., Lincolnshire, IL (US)

( * ) Notice: Subject to any disclaimer, the term of this patent is extended or adjusted under 35 U.S.C. 154(b) by 0 days.

(21) Appl. No.: 16/214,417

(22) Filed: Dec. 10, 2018

(65) Prior Publication Data

US 2019/0107533 A1    Apr. 11, 2019

Related U.S. Application Data

(63) Continuation of application No. 15/908,339, filed on Feb. 28, 2018, now Pat. No. 10,151,746, which is a
(Continued)

(30) Foreign Application Priority Data

Feb. 1, 2007 (JP) ................................ 2007-022523
Mar. 30, 2007 (JP) ................................ 2007-095226

(51) Int. Cl.
*G01N 15/06* (2006.01)
*G01N 35/00* (2006.01)
(Continued)

(52) U.S. Cl.
CPC ......... *G01N 33/5091* (2013.01); *G01N 15/12* (2013.01); *G01N 15/1459* (2013.01);
(Continued)

(58) Field of Classification Search
CPC ........ G01N 15/06; G01N 35/00; G01N 15/12; G01N 33/5091; G01N 33/5094;
(Continued)

(56) References Cited

U.S. PATENT DOCUMENTS 3,960,497 A    6/1976 Acord
4,001,584 A    1/1977 Mueller et al.
(Continued)

FOREIGN PATENT DOCUMENTS

CN    1591011 A    3/2005
CN    1281963 C    10/2006
(Continued)

OTHER PUBLICATIONS

Feb. 23, 2018 Response to notice of opposition—for EP Patent No. 1953527, dated Feb. 23, 2018, 26 pages.
(Continued)

*Primary Examiner* — Brian J. Sines
(74) *Attorney, Agent, or Firm* — Brinks Gilson & Lione

(57) ABSTRACT

A sample analyzer prepares a measurement sample from a blood sample or a body fluid sample which differs from the blood sample; measures the prepared measurement sample; obtains characteristic information representing characteristics of the components in the measurement sample; sets either a blood measurement mode for measuring the blood sample, or a body fluid measurement mode for measuring the body fluid sample as an operating mode; and measures the measurement sample prepared from the blood sample by executing operations in the blood measurement mode when the blood measurement mode has been set, and measuring the measurement sample prepared from the body fluid sample by executing operations in the body fluid measurement mode that differs from the operations in the blood measurement mode when the body fluid measurement mode
(Continued)

has been set, is disclosed. A computer program product is also disclosed.

28 Claims, 17 Drawing Sheets

Related U.S. Application Data continuation of application No. 14/595,319, filed on Jan. 13, 2015, now Pat. No. 9,933,414, which is a continuation of application No. 13/891,667, filed on May 10, 2013, now Pat. No. 8,968,661, which is a continuation-in-part of application No. 12/023,830, filed on Jan. 31, 2008, now Pat. No. 8,440,140.

(51) Int. Cl.
*G01N 15/12* (2006.01)
*G01N 33/50* (2006.01)
*G01N 15/14* (2006.01)
*G01N 33/72* (2006.01)
*G01N 15/00* (2006.01)

(52) U.S. Cl.
CPC ....... *G01N 33/5094* (2013.01); *G01N 33/721* (2013.01); *G01N 33/726* (2013.01); *G01N 2015/008* (2013.01); *G01N 2015/0073* (2013.01); *G01N 2015/0076* (2013.01); *G01N 2015/1486* (2013.01); *Y10T 436/11* (2015.01); *Y10T 436/113332* (2015.01)

(58) Field of Classification Search
CPC .. G01N 33/80; G01N 15/1459; G01N 33/721; G01N 33/726; G01N 33/728; G01N 2015/0065; G01N 2015/0073; G01N 2015/0076; G01N 2015/008; G01N 2015/1486; Y01T 436/11
USPC ....... 422/50, 68.1, 82.01, 82.05; 436/43, 47, 436/48, 49, 50, 63, 66, 174, 177, 178, 436/180
See application file for complete search history.

(56) References Cited

U.S. PATENT DOCUMENTS

| | | | |
|---|---|---|---|
| 4,303,337 A | 12/1981 | James et al. | |
| 4,564,598 A | 1/1986 | Briggs | |
| 5,122,453 A | 6/1992 | Martin et al. | |
| 5,132,087 A | 7/1992 | Manion et al. | |
| 5,138,181 A | 8/1992 | Lefevre et al. | |
| 5,288,374 A | 2/1994 | Watanabe et al. | |
| 5,555,196 A | 9/1996 | Asano | |
| 5,555,198 A | 9/1996 | Asano | |
| 5,812,419 A | 9/1998 | Chupp et al. | |
| 5,939,326 A | 8/1999 | Chupp et al. | |
| 6,060,022 A * | 5/2000 | Pang | G01N 35/0095 422/63 |
| 6,106,778 A | 8/2000 | Oku et al. | |
| 6,938,502 B2 | 9/2005 | Tanoshima et al. | |
| 6,979,570 B2 | 12/2005 | Narisada | |
| 7,141,213 B1 * | 11/2006 | Pang | G01N 35/0095 422/65 |
| 7,488,574 B2 | 2/2009 | Oguni | |
| 7,618,587 B2 | 11/2009 | Kawate | |
| 8,062,591 B2 | 11/2011 | Yamamoto | |
| 8,158,439 B2 | 4/2012 | Shibata | |
| 8,668,869 B2 | 3/2014 | Hirayama | |
| 2003/0030783 A1 | 2/2003 | Roche et al. | |
| 2003/0143117 A1 | 7/2003 | Nagai et al. | |
| 2003/0215890 A1 | 11/2003 | Ornstein et al. | |
| 2004/0101440 A1 | 5/2004 | Ishizawa et al. | |
| 2004/0156755 A1 | 8/2004 | Wardlaw | |
| 2005/0002552 A1 | 1/2005 | Dunn et al. | |
| 2005/0013737 A1 | 1/2005 | Chow et al. | |
| 2005/0053521 A1 | 3/2005 | Hirayama | |
| 2005/0176152 A1 * | 8/2005 | Lopez | G01N 15/12 436/63 |
| 2005/0196821 A1 | 9/2005 | Monfre et al. | |
| 2005/0219527 A1 | 10/2005 | Ikeuchi et al. | |
| 2005/0222504 A1 * | 10/2005 | Otvos | G01R 33/465 600/410 |
| 2006/0029520 A1 | 2/2006 | Tanoshima et al. | |
| 2006/0105462 A1 * | 5/2006 | Sellek-Prince | G01N 1/2813 436/55 |
| 2006/0160229 A1 * | 7/2006 | Lopez | G01N 15/12 436/63 |
| 2006/0189858 A1 * | 8/2006 | Sterling | A61B 5/14532 600/310 |
| 2006/0194325 A1 * | 8/2006 | Gable | A61B 5/0084 436/45 |
| 2006/0210438 A1 | 9/2006 | Nagai et al. | |
| 2007/0078631 A1 | 4/2007 | Ariyoshi et al. | |
| 2007/0105231 A1 * | 5/2007 | Riley | G01N 1/12 436/63 |
| 2007/0110617 A1 | 5/2007 | Nagai et al. | |
| 2008/0056944 A1 | 3/2008 | Nakamura et al. | |
| 2008/0187951 A1 | 8/2008 | Nagai et al. | |
| 2008/0206098 A1 | 8/2008 | Tsutsumida et al. | |
| 2008/0241911 A1 | 10/2008 | Ueno et al. | |
| 2008/0255705 A1 * | 10/2008 | Degeal | B07C 5/342 700/273 |
| 2008/0281471 A1 * | 11/2008 | Smith | B01F 13/0071 700/266 |
| 2009/0035873 A1 * | 2/2009 | Shibata | G01N 1/38 436/179 |
| 2009/0050821 A1 | 2/2009 | Tanaka et al. | |
| 2010/0234703 A1 | 9/2010 | Sterling et al. | |
| 2012/0232362 A1 * | 9/2012 | Gable | A61B 5/150755 600/310 |

FOREIGN PATENT DOCUMENTS

| | | |
|---|---|---|
| CN | 2837846 Y | 11/2006 |
| EP | 0 679 889 A2 | 11/1995 |
| EP | 0 679 889 A3 | 3/1996 |
| EP | 1 033 573 A2 | 9/2000 |
| EP | 1 033 573 A3 | 5/2003 |
| EP | 1 376 135 A2 | 1/2004 |
| JP | S58-114754 U | 8/1983 |
| JP | S60-73360 A | 4/1985 |
| JP | 62-150164 A | 7/1987 |
| JP | 02-287260 A | 11/1990 |
| JP | 05-018979 A | 1/1993 |
| JP | 5-133959 | 5/1993 |
| JP | 05-180831 A | 7/1993 |
| JP | H05-256852 A | 10/1993 |
| JP | H06-94676 | 4/1994 |
| JP | H06-207944 A | 7/1994 |
| JP | H07-003360 A | 1/1995 |
| JP | 10-221337 A | 8/1998 |
| JP | 2004-251802 A | 9/2004 |
| JP | 2006-292738 A | 10/2006 |

OTHER PUBLICATIONS

First auxiliary request (marked up)—for EP Application No. 08001713.0, dated Feb. 23, 2018, 7 pages.
Second auxiliary request (marked up)—for EP Application No. 08001713.0, dated Feb. 23, 2018, 16 pages.
Third auxiliary request (marked up)—for EP Application No. 08001713.0, dated Feb. 23, 2018, 8 pages.
Fourth auxiliary request (marked up)—for EP Application No. 08001713.0, dated Feb. 23, 2018, 8 pages.
Fifth auxiliary request (marked up)—for EP Application No. 08001713.0, dated Feb. 23, 2018, 9 pages.
Sixth auxiliary request (marked up)—for EP Application No. 08001713.0, dated Feb. 23, 2018, 8 pages.
Seventh auxiliary request (marked up) —for EP Application No. 08001713.0, dated Feb. 23, 2018.

(56) References Cited

OTHER PUBLICATIONS

Jun. 14, 2018—Letter to EPO for EP Patent No. 1953527, dated Jun. 14, 2018, 2 pages.
Jun. 26, 2018—Letter to EPO for EP Patent No. 1953527, dated Jun. 26, 2018, 2 pages.
Sep. 11, 2018—Letter to EPO for EP Patent No. 1953527, dated Sep. 11, 2018, 30 pages.
Amended claims (mark-up)—auxiliary request 8—for EP Application No. 08001713.0 dated Sep. 11, 2018.
Nov. 7, 2018—Letter to EPO for EP Patent No. 1953527, dated Nov. 7, 2018, 6 pages.
Jan. 2, 2019 Submission in opposition proceedings—for EP Patent No. 1953527, dated Jan. 2, 2019, 49 pages.
Auxiliary request 0A—for EP Application No. 08001713.0 dated Jan. 2, 2019, 7 pages.
Auxiliary request 0B—for EP Application No. 08001713.0 dated Jan. 2, 2019, 7 pages.
Auxiliary request 0C—for EP Application No. 08001713.0 dated Jan. 2, 2019, 7 pages.
Auxiliary request 0D—for EP Application No. 08001713.0 dated Jan. 2, 2019, 7 pages.
Auxiliary request 1A—for EP Application No. 08001713.0 dated Jan. 2, 2019, 7 pages.
Auxiliary request 1B—for EP Application No. 08001713.0 dated Jan. 2, 2019, 7 pages.
Auxiliary request 1C—for EP Application No. 08001713.0 dated Jan. 2, 2019, 7 pages.
Auxiliary request 1D—for EP Application No. 08001713.0 dated Jan. 2, 2019, 7 pages.
Auxiliary request 2A—for EP Application No. 08001713.0 dated Jan. 2, 2019, 16 pages.
Auxiliary request 2B—for EP Application No. 08001713.0 dated Jan. 2, 2019, 16 pages.
Auxiliary request 2C—for EP Application No. 08001713.0 dated Jan. 2, 2019, 16 pages.
Auxiliary request 2D—for EP Application No. 08001713.0 dated Jan. 2, 2019, 16 pages.
Auxiliary request 3A—for EP Application No. 08001713.0 dated Jan. 2, 2019, 7 pages.
Auxiliary request 3B—for EP Application No. 08001713.0 dated Jan. 2, 2019, 16 pages.
Auxiliary request 3C—for EP Application No. 08001713.0 dated Jan. 2, 2019, 16 pages.
Auxiliary request 3D—for EP Application No. 08001713.0 dated Jan. 2, 2019, 16 pages.
Auxiliary request 4A—for EP Application No. 08001713.0 dated Jan. 2, 2019, 7 pages.
Auxiliary request 4B—for EP Application No. 08001713.0 dated Jan. 2, 2019, 7 pages.
Auxiliary request 4C—for EP Application No. 08001713.0 dated Jan. 2, 2019, 7 pages.
Auxiliary request 4D—for EP Application No. 08001713.0 dated Jan. 2, 2019, 7 pages.
Auxiliary request 4E—for EP Application No. 08001713.0 dated Jan. 2, 2019, 7 pages.
Auxiliary request 4F—for EP Application No. 08001713.0 dated Jan. 2, 2019, 7 pages.
Auxiliary request 4G—for EP Application No. 08001713.0 dated Jan. 2, 2019, 7 pages.
Auxiliary request 4H—for EP Application No. 08001713.0 dated Jan. 2, 2019, 7 pages.
Auxiliary request 4I—for EP Application No. 08001713.0 dated Jan. 2, 2019, 7 pages.
Auxiliary request 5A—for EP Application No. 08001713.0 dated Jan. 2, 2019, 8 pages.
Auxiliary request 5B—for EP Application No. 08001713.0 dated Jan. 2, 2019, 8 pages.
Auxiliary request 5C—for EP Application No. 08001713.0 dated Jan. 2, 2019, 8 pages.
Auxiliary request 5D—for EP Application No. 08001713.0 dated Jan. 2, 2019, 8 pages.
Auxiliary request 6A—for EP Application No. 08001713.0 dated Jan. 2, 2019, 7 pages.
Auxiliary request 6B—for EP Application No. 08001713.0 dated Jan. 2, 2019, 7 pages.
Auxiliary request 6C—for EP Application No. 08001713.0 dated Jan. 2, 2019, 7 pages.
Auxiliary request 6D—for EP Application No. 08001713.0 dated Jan. 2, 2019, 7 pages.
Auxiliary request 7A—for EP Application No. 08001713.0 dated Jan. 2, 2019, 7 pages.
Auxiliary request 7B—for EP Application No. 08001713.0 dated Jan. 2, 2019, 7 pages.
Auxiliary request 7C—for EP Application No. 08001713.0 dated Jan. 2, 2019, 7 pages.—for EP Application No. 08001713.0 dated Jan. 2, 2019, 7 pages.
Auxiliary request 7D—for EP Application No. 08001713.0 dated Jan. 2, 2019, 7 pages.
Auxiliary request 8A—for EP Application No. 08001713.0 dated Jan. 2, 2019, 7 pages.
Auxiliary request 8B—for EP Application No. 08001713.0 dated Jan. 2, 2019, 7 pages.
Auxiliary request 8C—for EP Application No. 08001713.0 dated Jan. 2, 2019, 7 pages.
Auxiliary request 8D—for EP Application No. 08001713.0 dated Jan. 2, 2019, 7 pages.
D34 declaration by Alberto Bonacini—in Opposition against EP Patent No. 1953527, dated Nov. 28, 2018, 3 pages.
D35 Technical testing of a Beckman Coulter LH750, dated Oct. 18, 2018, 13 pages.
Feb. 8, 2019—Letter to EPO for EP Patent No. 1953527, dated Feb. 8, 2019, 28 pages.
Amended claims—auxiliary request 4D1 mark-up—for EP Patent No. 1953527, dated Feb. 8, 2019, 8 pages.
Amended claims—auxiliary request 4I1 mark-up—for EP Patent No. 1953527, dated Feb. 8, 2019, 8 pages.
Amended claims—auxiliary request 5D1 mark-up—for EP Patent No. 1953527, dated Feb. 8, 2019, 8 pages.
Amended claims—auxiliary request 8D1 mark-up—for EP Patent No. 1953527, dated Feb. 8, 2019, 8 pages.
D38 with sticker—Webster's New Encyclopedic Dictionary cited in Opposition against EP Patent No. 1953527, 1996, 3 pages.
D39 with sticker—Confirm—Wiktionary—dated Jan. 24, 2007, 2 pages.
D40 with sticker—The American Heritage dictionary, 2019, 3 pages.
Oct. 11, 2017 Notice of opposition—dated Oct. 11, 2017, 38 pages.
D1 the European Application as filed—dated Jan. 30, 2008, EP Application No. 08001713.0, 70 pages.
D2 Coulter® LH700 Series Body Fluids Application Operator's Guide 731113A (Sep. 2004), 48 pages.
D3 Coulter® LH700 Series System Reference manual 4277248C (Oct. 2003), 114 pages.
D8 English translation of priority document JP2007022523, date of application Feb. 1, 2007, 35 pages.
D9 English translation of priority document JP2007095226, date of application Mar. 30, 2007, 35 pages.
D16c Change Notice regarding D3 release dated Nov. 5, 2003, 2 pages.
D16d Change Notice regarding D2 release dated Dec. 13, 2004, 2 pages.
Jun. 4, 2018 additional submission—EP Patent No. 1953527, dated Jun. 4, 2018, 2 pages.
Notice of intervention to a European patent—EP Patent No. 1953527, dated Jun. 1, 2018, 8 pages.
Arguments against patent EP1953527B1 dated Jun. 1, 2018, 66 pages.
D18 Complaint of Sysmex Corporation filed to Mannheim, dated Feb. 23, 2018, 68 pages.
D18a Confirmation of the receipt of D18 by the opponent, dated Mar. 2, 2018, 1 page.
D18b register of DPMA, dated Jan. 27, 2018, 2 pages.

(56) References Cited

OTHER PUBLICATIONS

D19a JP6-94676, dated Apr. 8, 1994.
D19b certified English translation of JP6-, dated Apr. 8, 1994.
D19c Translation certificate, dated Apr. 8, 1994.
D20 DE4330741 (familiy of JP6-94676), dated Mar. 17, 1994, including English Abstract.
D25 2nd Declaration of Douglas Drew Dunbabin, dated May 24, 2018, 2 pages.
D26 2nd Declaration Jonna Scott, dated May 30, 2018, 1 page.
D29 Declaration of Eric Grace, dated May 23, 2018, 3 pages.
D30 Annex 1 of Declaration of Eric Grace (list of LH750 customers), dated May 23, 2018, 3 pages.
Jun. 21, 2018—Response to Official Communication in EP 08001713.0, dated Jun. 21, 2018, 5 pages.
Jul. 11, 2018—Response to Official Communication in EP 08001713.0, dated Jul. 11, 2018, 4 pages.
D27 Declaration of Beverly Colbert, dated Jul. 7, 2018, 9 pages.
D28 "Body fluid cell count, automated coulter LH750" referred to by Beverly Colbert, Revised date Dec. 6, 2006 and Feb. 8, 2008, 7 pages.
Sep. 12, 2018—Response to Patentee's Submission, dated Sep. 12, 2018, 32 pages.
D32 XE-2100, Copyright 2001-2004, 125 pages.
D33 XE-5000, date revised Dec. 2006, 265 pages.
Jan. 4, 2019—Response to 2nd Summons, in EP 08001713.0, dated Jan. 4, 2018, 51 pages.
D34 Body Fluids 3rd edition, Kjeldsberg, et al., date copyright 1993, 23 pages.
D35 Declaration of Eric Grace, dated Dec. 21, 2018, 4 pages.
D36 Service report, dated Jan. 2006, 6 pages.
D37 Examination decision CN Appln. 200810005238.8 dated Dec. 14, 2018, 37 pages.
May 8, 2018 preliminary opinion (1st), in EP 08001713.0 dated May 8, 2018, 18 pages.
Oct. 8, 2018 preliminary opinion (2nd), in EP 08001713.0 dated Oct. 8, 2018, 27 pages.
Jun. 5, 2018—Patentee's Response to Request for Invalidity Trial, including English Translation, dated Jun. 5, 2018, 58 pages.
Sep. 28, 2018 Opinions Statement by Patentee in Trial for Invalidation Procedures, English Translation thereof—dated Sep. 28, 2018, 17 pages.
Jan. 3, 2019 Administrative complaint, English Translation thereof—dated Jan. 3, 2019, 7 pages.
Apr. 20, 2018—Request for Invalidity Trial for CN Patent No. 200810005238.8, including English Translation, dated Apr. 20, 2018, 30 pages.
May 21, 2018—Supplementary Opinion in CN 200810005238.8, including English Translation, dated May 21, 2018, 106 pages.
Dec. 14, 2018 Examination Decision for Invalidation Announcement Request in CN 200810005238.8, English Translation, dated Dec. 14, 2018, 34 pages.
Cerebrospinal Fluid Cell Fractionation Assay by Automated Blood Cell Measuring Apparatus—CSF Assay by ADVIA 120/120, Apr. 2005.
"Coulter® LH 700 Series System", Beckman Coulter, Oct. 2003, 114 pages.
"Coulter® LH Series Workstation Body Fluid Application—Operator's Guide", Beckman Coulter, Sep. 2004, 48 pages.
510(k) Summary of the XE-5000, *Sysmex America, Inc.*, 2007, 20 pages.
Aulesa, C, et al., "Use of the Advia 120 Hematology Analyzer in the Differential Cytologic Analysis of Biological Fluids (Cerebrospinal, Peritoneal, Pleural, Pericardial, Synovial, and Others)", *Laboratory Hematology*, vol. 9, 2003, pp. 214-224.
Kresie, L. et al,, "Performance Evaluation of the Application of Body Fluids on the Sysmex XE-2100 Series Automated Hematology Analyzer", *Laboratory Hematology*, vol. 11, 2005, pp. 24-30.
Harris, N. et al,, "Perfomance Evaluation of the ADVIA 2120 Hematology Analyzer: An International Multicenter Clinical Trial", *Laboratory Hematology*, vol. 11, 2005, pp. 62-70.
Andrews, J. et al., "An Evaluation of the Cell-Dyn 3200 for Counting Cells in Cerebrospinal and Other Bodily Fluids", *Laboratory Hematology*, vol. 11, 2005, pp. 98-106.
Brown. W,, "Validation of Body Fluid Analysis on the Coulter LH750", *Laboratory Hematology*, vol. 9, 2003, pp. 155-159.
"Declaration of Douglas Drew Dunbabin, in the matter of European Patent No. EP 1 953 527", Oct. 10, 2017, 22 pages.
"Declaration of Jonna Scott, in the matter of European Patent No. EP 1 953 527", Oct. 10, 2017, 2 pages.
Harris, N, et al., "Performance Evaluation of the ADVIA 2120 Hematology Analyzer: An International Multicenter Clinical Trial", *Laboratory Hematology*, vol. 11, 2005, pp. 62-70.
Technical Update, "LH 750 Body Fluids Application, Software Revisions 2B3 and 2C2", Beckman Coulter, Jan. 31, 2005, 1 page.
Technical Update, "LH 750 Body Fluids Application, Software Revisions 2B3 and 2C2", Beckman Coulter, Jan. 31, 2005, 14 pages.
"Change Notice Regarding Coulter LH700 Series System Reference Manual", Beckman Coulter, Nov. 5, 2003, 2 pages.
"Change Notice Regardnig Coulter LH700 Series Body Fluids Application Operator's Guide", Beckman Coulter, Dec. 13, 2004, 2 pages.
Hoffman et al., "Automated Counting of Cells in Cerebrospinal Fluid Using the CellDyn-4000 Haematology Analyser" Clin. Chem. Lab Med 2002, vol. 40, No. 11, pp. 1168-1173, Berlin, New York.
Curriculum Vitae of Douglas Drew Dunbabin, 2 pages, dated Oct. 11, 2017.
ES66 Feb. 26, 2019 submission, in EP Patent No. 1953527, 2 pages, dated Feb. 26, 2019.
ES67 Feb. 28, 2019 submission, in EP Patent No. 1953527, 4 pages, dated Feb. 28, 2019.
ES68 Mar. 8, 2019 submission EPO, in EP Patent No. 1953527, 3 pages, dated Mar. 8, 2019.
ES69 Mar. 14, 2019 Submissions as filed, in EP Patent No. 1953527, 6 pages, dated Mar. 14, 2019.
ES70 Mar. 15, 2019_Submissions as filed, in EP Patent No. 1953527, 4 pages, dated Mar. 15, 2019.
ES71 Mar. 18, 2019_Submissions as filed, in EP 1953527, 4 pages, dated Mar. 18, 2019.
EB26-2 Arguments against patent EP1953527B1 dated Jun. 1, 2018, 71 pages.
EB42 D31 Feature analysis of claims 1 and 20, dated Jun. 1, 2018, 2 pages.
EB48-2 D32 XE-2100, Copyright 2001-2004, 130 pages.
EB55 Feb. 21, 2019 Submission, in EP Patent No. 1953527, 7 pages, dated Feb. 21, 2019.
EB56 EP1953527 D41, including English Translation, 62 pages, dated Oct. 22, 2018.
EB57 Mar. 12, 2019 first letter BC Inc, in EP Patent No. 1953527, 3 pages, dated Mar. 12, 2019.
EB58 Mar. 12, 2019 second letter BC Inc, in EP Patent No. 1953527, 1 page, dated Mar. 12, 2019.
EB59 Mar. 12, 2019 first letter BC GmbH, in EP Patent No. 1953527, 3 pages, dated Mar. 12, 2019.
EB60 Mar. 12, 2019 second letter BC GmbH, in EP Patent No. 1953527, 1 page, dated Mar. 12, 2019.
EP3 Mar. 7, 2019 Information about the result of oral proceedings, in EP Appl. No. 08001713.0, 9 pages, dated Mar. 7, 2019.
EP4 Consolidated list of filed evidence, 4 pages, dated Mar. 7, 2019.
CS2-2 Jul. 19, 2018, Observations of Patentee in the Invalidation Proceeding, including English Translation, 182 pages, dated Jul. 19, 2018.
CB12 Aug. 3, 2018, Observation, including English Translation, in CN Patent No. 200810005238.8, 25 pages, dated Aug. 3, 2018.
ES72 Mar. 20, 2019 submission, 1 page, dated Mar. 20, 2019.
ES73 Mar. 27, 2019 submission, 6 pages, dated Mar. 27, 2019.
ES74 Apr. 18, 2019 submission as filed, 4 pages, dated Apr. 18, 2019.
ES75 Apr. 24, 2019 request for correction of the minutes (as filed), 4 pages, dated Apr. 24, 2019.
EB61 Mar. 19, 2019 Letter from BC GmbH, 5 pages, dated Mar. 19, 2019.

(56) References Cited

OTHER PUBLICATIONS

EB62 Mar. 19, 2019 Letter from BC Inc, 5 pages, dated Mar. 19, 2019.
EB63 Teschemacher—list of publications, 4 pages, dated Mar. 19, 2019.
EB64 CV Teschemacher, 1 page, dated Mar. 19, 2019.
EB65 D44, 9 pages, dated Mar. 19, 2019.
EP5 Apr. 17, 2019 minutes, 14 pages, dated Apr. 17, 2019.
EP6 Apr. 17, 2019 Annex to the minutes—AR44 which became AR2, 8 pages, dated Apr. 17, 2019.
EP7 Apr. 17, 2019 Annex to the minutes—consolidated list of filed evidence, 4 pages, dated Apr. 17, 2019.
ES76 May 8, 2019 submission EPO, 4 pages, dated May 8, 2019.
EB66 Apr. 18, 2019 submission by BC, 4 pages, dated Apr. 18, 2019.
EP8 May 14, 2019 communication pursuant to Article 101(1) and Rule 81(2) to (3) EPC, 4 pages, dated May 14, 2019.
EB63 Teschemacher—list of publications, 4 pages, dated Mar. 19, 2019, including partial English translation.
EB64 CV Teschemacher, 3 pages, dated Mar. 19, 2019, including English translation.
EB65 D44, 15 pages, dated Mar. 19, 2019, including English translation.

\* cited by examiner

| Manual | Next No. | 1 | Num |
|---|---|---|---|
| CDNR | OP No. | | OP |
| Measurement not possible | | | Xm |
| <manual sample number input> ||||
| Sample number | | 1 | |
| Mode  1  2  3<br>manual capillary closed ||||
| Discrete<br>  1   2   3   4   5   6   7<br>CBC CBC CBC CBC CBC CBC CBC<br>         DIFF DIFF     DIFF DIFF<br>     NRBC                NRBC NRBC<br>               RET RET        RET ||||
| Sample 1 : Normal  2 : HPC  3 : Body Fluid ||||

120 — <manual sample number input>
121 — Mode
122 — Discrete
123 — Sample

Fig.8

| Example 1 | | | Example 2 | | | Example 3 | | |
|---|---|---|---|---|---|---|---|---|
| | Ref | This Method | | Ref | This Method | | Ref | This Method |
| WBC | 4580 | 4364 | WBC | 1370 | 1160 | WBC | 1360 | 1391 |
| Others | 1420 | 1387 | Others | 670 | 535 | Others | 70 | 74 |

SAMPLE ANALYZER AND COMPUTER PROGRAM PRODUCT

This application is a Continuation of U.S. application Ser. No. 15/908,339 filed Feb. 28,2018, which is a Continuation of U.S. application Ser. No. 14/595,319 filed Jan. 13, 2015, now U.S. Pat. No. 9,933,414, which is a Continuation of U.S. application Ser. No. 13/891,667 filed May 10, 2013, now U.S. Pat. No. 8,968,661, which is a Continuation of U.S. application Ser. No. 12/023,830 filed Jan. 31, 2008, now U.S. Pat. No. 8,440,140, claiming priority to Japanese Application No. 2007-022523 filed on Feb. 1, 2007 and to Japanese Application No. 2007-095226 filed on Mar. 30, 2007, all of which are incorporated herein by reference in their entireties.

FIELD OF THE INVENTION

The present invention relates to a sample analyzer and a computer program product capable of measuring not only blood, but also body fluids other than blood such as cerebrospinal fluid (spinal fluid), fluid of the thoracic cavity (pleural fluid), abdominal fluid and the like.

BACKGROUND

In the field of clinical examinations, blood is routinely collected from a body and used as a sample which is measured by a sample analyzer to aid diagnosis and monitor treatment. Furthermore, body fluids other than blood are also often used as samples which are measured by a sample analyzer. The body fluids are usually transparent and contain very few cells, however, cells such as bacteria, abnormal cells, and hemorrhage (blood cells) and the like may be found in cases of disease, tumors of related organs, and injury.

When cerebrospinal fluid, which is one type of body fluid, is measured, for example, it is possible to make the following estimations from the measurement results.

Increase of red blood cells: subarachnoidal hemorrhage
Increase of neutrophils: meningitis
Increase of eosinophils: infectious disease (parasites and fungus)
Increase of monocytes: tuberculous meningitis, viral meningitis
Other cells: advanced meningeal tumor Japanese Laid-Open Patent Publication No. 2003-344393 discloses a blood cell analyzer which is capable of measuring cells in a body fluid. In Japanese Laid-Open Patent Publication No. 2003-344393, an operator prepares a measurement sample prior to performing the measurements by mixing a fluid sample and reagent (aldehyde, surface active agent, and cyclodextrin) in order to stably store the body fluid for a long period, and this measurement sample is later subjected to fluid analysis by the sample analyzer.

In the art of Japanese Laid-Open Patent Publication No. 2003-344393, however, the measurement sample is not prepared by the sample analyzer when the body fluid is measured, rather the measurement sample must be prepared by the operator of the analyzer. Furthermore, the sample analyzer disclosed in Japanese Laid-Open Patent Publication No. 2003-344393 does not disclose measurement operations suited to the fluid when measuring a body fluid.

SUMMARY OF THE INVENTION

The scope of the present invention is defined solely by the appended claims, and is not affected to any degree by the statements within this summary.

A first aspect of the present invention is a sample analyzer comprising: a measuring part for preparing a measurement sample from a blood sample, or a body fluid sample that differs from the blood sample, measuring the prepared measurement sample, and obtaining characteristic information representing characteristics of components within the measurement sample; a mode setting means for setting either a blood measurement mode for measuring the blood sample, or a body fluid measurement mode for measuring the body fluid sample as an operating mode; a first control means for controlling the measuring part so as to execute operations in the blood measurement mode when the blood measurement mode has been set by the mode setting means; and a second control means for controlling the measuring part so as to execute operations in the body fluid measurement mode which differs from the operations in the blood measurement mode when the body fluid measurement mode has been set by the mode setting means.

A second aspect of the present invention is a sample analyzer comprising: a measuring part for preparing a measurement sample from a blood sample or a body fluid sample that differs from the blood sample, measuring the prepared measurement sample, and obtaining characteristic information representing characteristics of components within the measurement sample; a mode setting means for setting either a blood measurement mode for measuring the blood sample, or a body fluid measurement mode for measuring the body fluid sample as an operating mode; a first analyzing means for executing a first analysis process based on the characteristic information obtained by measuring the measurement sample prepared by the measuring part from the blood sample when the blood measurement mode has been set by the mode setting means; and a second analyzing means for executing a second analysis process which differs from the first analysis process based on the characteristic information obtained by measuring the measurement sample prepared by the measuring part from the body fluid sample when the body fluid measurement mode has been set by the mode setting means.

A third aspect of the present invention is a sample analyzer comprising: a measuring part for preparing a measurement sample from a blood sample or a body fluid sample that differs from the blood sample, measuring the prepared measurement sample, and obtaining characteristic information representing characteristics of components within the measurement sample; a mode switching means for switching an operating mode from a blood measurement mode for measuring the blood sample to a body fluid measurement mode for measuring the body fluid sample; and a blank measurement controlling means for controlling the measuring part so as to measure a blank sample that contains neither the blood sample nor the body fluid sample when the mode switching means has switched the operating mode from the blood measurement mode to the body fluid measurement mode.

A fourth aspect of the present invention is a computer program product, comprising: a computer readable medium; and instructions, on the computer readable medium, adapted to enable a general purpose computer to perform operations, comprising: a step of preparing a measurement sample from a blood sample or a body fluid sample which differs from the blood sample; a step of measuring the prepared measurement sample; a step of obtaining characteristic information representing characteristics of the components in the measurement sample; a step of setting either a blood measurement mode for measuring the blood sample, or a body fluid measurement mode for measuring the body fluid sample as an operating mode; and a step of measuring the measurement sample prepared from the blood sample by executing operations in the blood measurement mode when the blood measurement mode has been set, and measuring the measurement sample prepared from the body fluid sample by executing operations in the body fluid measurement mode that differs from the operations in the blood measurement mode when the body fluid measurement mode has been set.

BRIEF DESCRIPTION OF THE DRAWINGS

FIG. 8 shows the display screen for setting the measurement mode;
FIG. 11 compares measurement results by the blood cell analyzer of the embodiment and measurement results by a reference method;
FIG. 16 is a display screen showing the measurement results in the body fluid measurement mode.

DETAILED DESCRIPTION OF THE PREFERRED EMBODIMENTS

Figure 1:
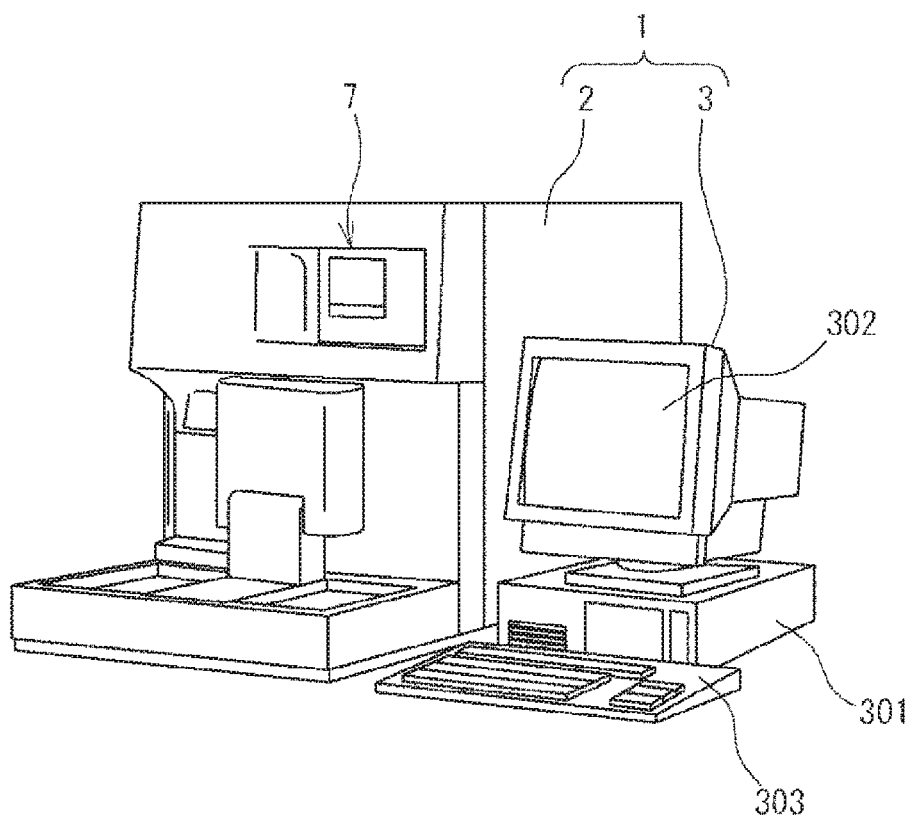
FIG. 1 is an exterior view of a blood cell analyzer of a first embodiment of the present invention.

The preferred embodiments of the present invention will be described hereinafter with reference to the drawings.
FIG. 1 shows a sample analyzer 1. The sample analyzer 1 is configured as an automatic multi-item blood cell analyzer which performs blood analysis by measuring blood samples held in sample containers (blood collection tubes), obtaining characteristics information representing the characteristics of the blood cells contained in the sample, and analyzing the characteristic information. The sample analyzer 1 is also capable of analyzing body fluids. In the blood cell analyzer of the present embodiment, the body fluids used as analysis objects include, fluid within the body cavity other than blood. Specifically, cerebrospinal fluid (spinal fluid, CSF: fluid filling the ventricle or sublemmal cavity), fluid of the thoracic cavity (pleural fluid, PE: fluid collected in pleural cavity), abdominal fluid (fluid collected in the abdominal cavity), fluid of the cardiac sac (fluid collected in the cardiac sac), synovial fluid (fluid present in joints, synovial sac, peritenon) and the like. Among types of body fluid which can be analyzed are dialysate of peritoneal dialysis (CAPD), intraperitoneal rinse and the like. Cells are usually not observed in these body fluids, however, the fluids may contain blood cells, abnormal cells, and cells such as bacteria in the case of disease, tumor of related organs, or injury. For example, it is possible to clinically estimate the following from measurement results in the case of cerebrospinal fluid. For example, subarachnoidal hemorrhage is indicted when there is an increase of red blood cells, meningitis is indicated when there is an increase of neutrophils, infectious disease (parasitic and fungal) is indicated when there is an increase of eosinophils, tuberculous meningitis and viral meningitis are indicated when there is an increase of monocytes, and advanced meningeal tumor is indicated when there is an increase of other cells. ed In the case of abdominal and thoracic fluids, cancers may be indicated when analysis of finds nucleated cells other than blood cells, that is, the fluid contains nucleated cells of mesothelial cells, macrophages, tumor cells and the like.

The sample analyzer 1 is provided with a measuring unit 2 which has the function of measuring blood and body fluid samples, and a data processing unit 3 which obtains analysis results by processing the measurement results output from the measurement unit 2. The data processing unit 3 is provided with a control unit 301, a display unit 302, and an input unit 303. Although the measuring unit 2 and data processing unit 3 are separate devices in FIG. 1, the both may also be integrated in a single apparatus.

Figure 2:
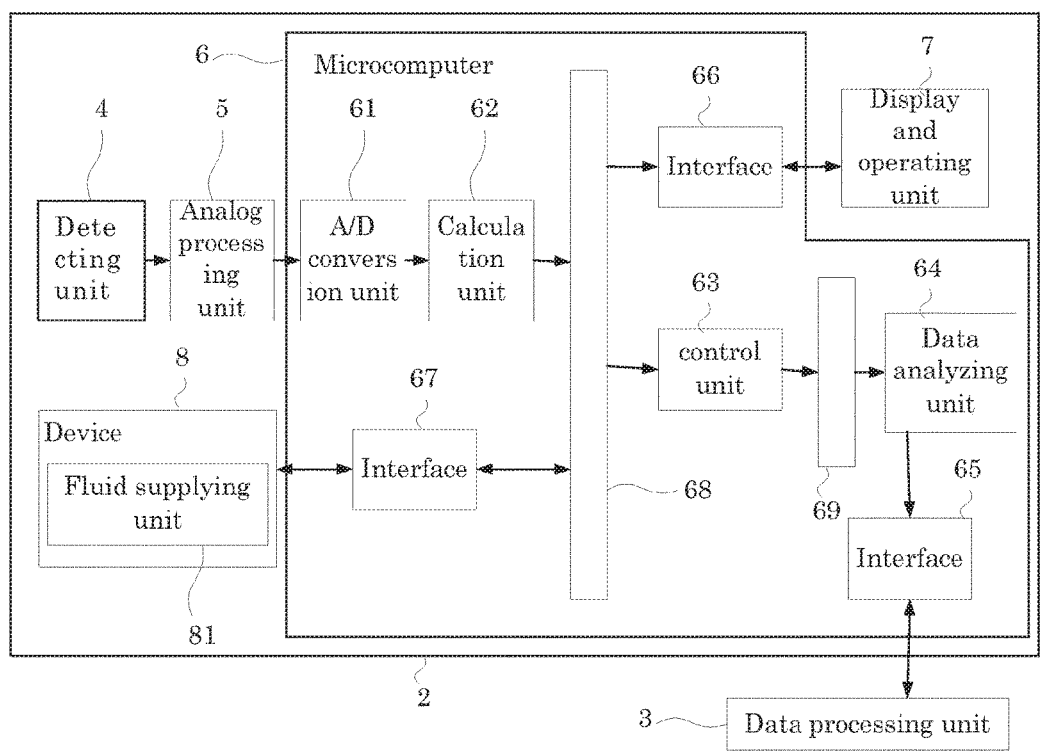
FIG. 2 is a block diagram of the measuring unit of the analyzer.

FIG. 2 is a block diagram of the measuring unit 2 of the analyzer 1. As shown in FIG. 2, the measuring unit 2 is provided with a blood cell detecting unit 4, an analog processing unit 5 which processes the output (analog signals) of the detecting unit 4, microcomputer unit 6, display and operating unit 7, and a device 8 for measuring blood and body fluids. The device 8 includes a fluid supplying unit 81 which is described below.

Figure 3:
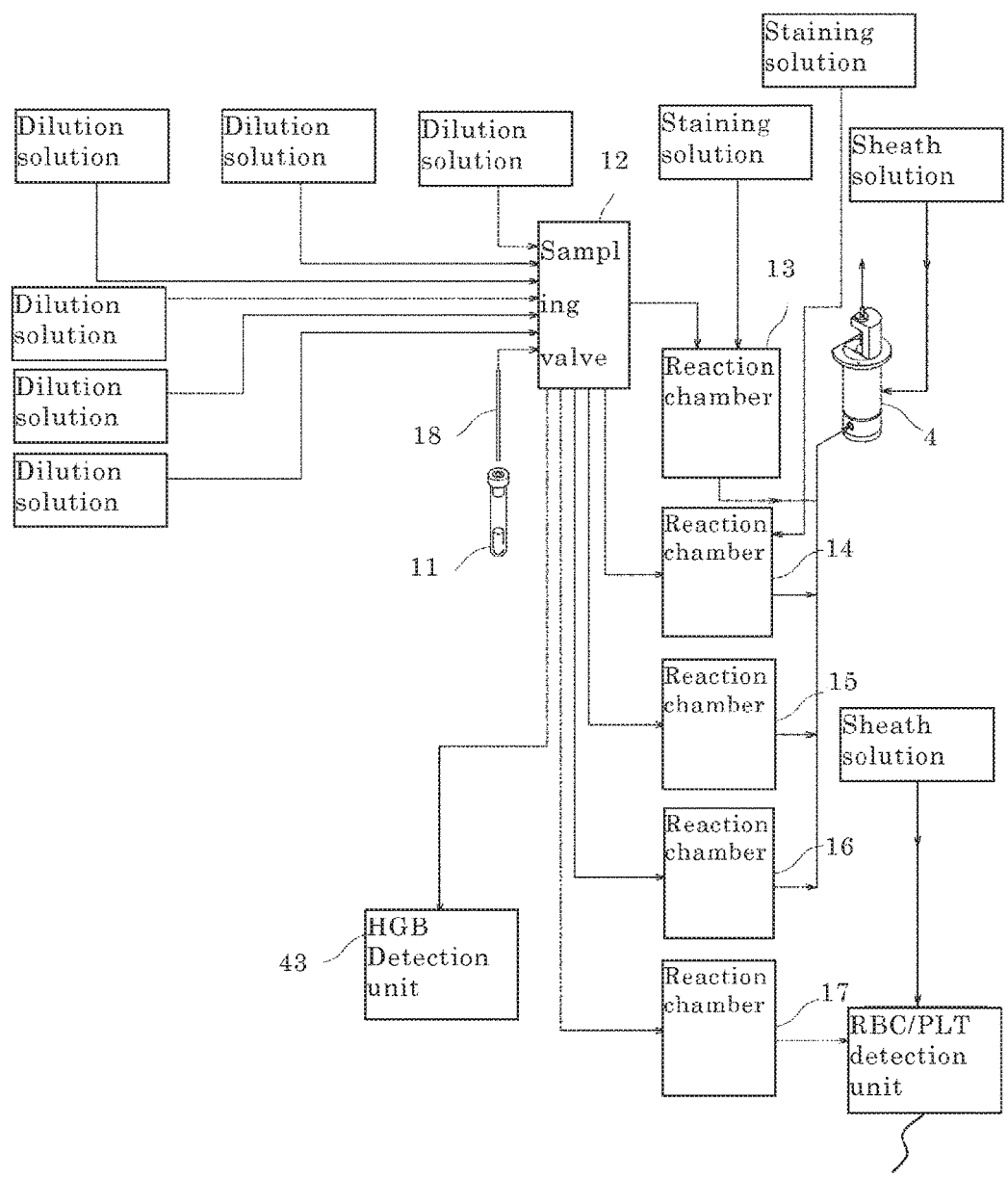
FIG. 3 is a block diagram of the fluid supplying unit.

FIG. 3 is a block diagram showing the structure of the fluid supplying unit 81. As shown in FIG. 3, the fluid supplying unit 81 is provided with a sample aspiration nozzle 18, a plurality of reagent containers, a sampling valve 12, and reactions chambers 13 through 17. The sample aspiration nozzle 18 aspirates sample from a sample container, and delivers the sample to the sampling valve 12. The sampling valve 12 divides the delivered sample into several aliquots of predetermined volume. The number of divisions differs depending on the mode of measurement (discrete mode); in the CBC mode the sample is divided into three aliquots to measure the number of red blood cells, the number of white blood cells, the number of platelets, and the hemoglobin concentration. In addition to the CBC measurement items, the sample is divided into four aliquots in the CBC-DIFF mode so as to also classify five types of white blood cells. Furthermore, In addition to the measurement items of the CBC+DIFF mode, the sample is divided into five aliquots in the CBC+DIFF+RET mode so as to also measure reticulocytes.

Similarly, in addition to the measurement items of the CBC+DIFF mode, the sample is divided into five aliquots in the CBC+DIFF+NRBC mode so as to also measure nucleated red blood cells. In addition to the measurement items of the CBC+DIFF+RET mode, the sample is divided into six aliquots in the CBC+DIFF+RET+NRBC mode so as to also measure nucleated red blood cells. The above mentioned measurement modes are blood measuring modes which measure whole blood. Finally, the sample is divided into two aliquots in the body fluid measuring mode for measuring body fluid.

Reagent (dilution solution) is introduced from a reagent container to the sampling valve, and the aliquots of the divided sample are delivered together with the reagent to the reaction chambers 13 through 17 and an HGB detection unit 43, which is described later, a predetermined amount of sample (aliquot) and a predetermined amount of reagent and a predetermined amount of stain collected by the sampling valve 12 are supplied to the reaction chamber 13 by a dosage pump which is not shown in the drawing, the sample and reagent are mixed to prepare a measurement sample for four classifications of white blood cells (DIFF).

The reagent "stomatolyzer 4DL" made by Sysmex Corporation may be used as the dilution solution. This reagent contains surface active agent and induces hemolysis of red blood cells. The reagent "stomatolyzer 4DS" made by Sysmex Corporation may be used as the stain. This stain contains ethylene glycol, low molecular alcohol, and polymethene colorant; a 50× dilute sample is ultimately prepared by staining the blood cell component after hemolysis by the dilution agent.

When the body fluid measurement mode has been selected, a measurement sample for the classification of white blood cells is prepared from a fluid sample under the conditions of the amount of the sample and reagent used for the four classifications of white blood cells are identical, the reagents are identical, and the amounts of the reagent are identical. In the white blood cell classification of the body fluid measurement mode, the white blood cells are classified, not in four types, but two types, as shall be described later.

A predetermined amount of sample collected by the sampling valve 12, a predetermined amount of hemolytic dilution agent, and a predetermined amount of stain solution are supplied to the reaction chamber 14 by a dosage pump which is not shown in the drawing, the sample and reagents are then mixed to prepare a measurement sample for measuring nucleated red blood cells (NRBC).

A predetermined amount of sample collected by the sampling valve 12, a predetermined amount of dilution agent, and a predetermined amount of stain solution are supplied to the reaction chamber 15 by a dosage pump which is not shown in the drawing, the sample and reagents are then mixed to prepare a measurement sample for measuring reticulocytes (RET).

A predetermined amount of sample collected by the sampling valve 12, and a predetermined amount of hemolytic dilution agent are supplied to the reaction chamber 16 by a dosage pump which is not shown in the drawing, the sample and reagents are then mixed to prepare a measurement sample for measuring white blood cells and basophils (WBC/BASO).

A predetermined amount of sample collected by the sampling valve 12, and a predetermined amount of dilution solution are supplied to the reaction chamber 17 by a dosage pump which is not shown in the drawing, the sample and reagents are then mixed to prepare a measurement sample for measuring red blood cells and platelets (RBC/PLT).

A predetermined amount of sample collected by the sampling valve 12, and a predetermined amount of hemolytic dilution agent are supplied to the HGB detection unit 43 which is described later.

The detection device 4 is provided with a white blood cell detection unit 41 for detecting white blood cells. The white blood cell detection unit 41 is also used to detect nucleated red blood cells and reticulocytes. In addition to the white blood cell detection unit, the detection device 4 is also provided with an RBC/PLT detection unit 42 for measuring the number of red blood cells and the number of platelets, and an HGB detection unit 43 for measuring the amount of pigment in the blood.

Figure 4:
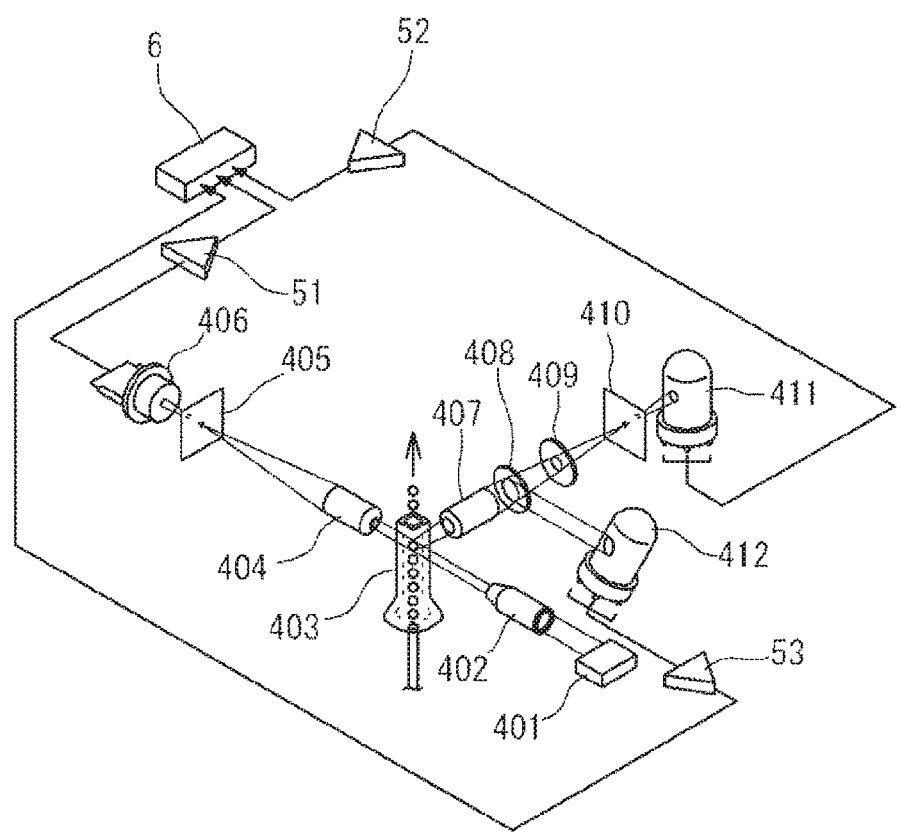
FIG. 4 shows the optical system of the white blood cell detection unit.

The white blood cell detection unit 41 is configured as an optical detection unit, specifically, a detection unit which uses a flow cytometric method. Cytometry measures the optical properties and physical properties of cells and other biological particles, and flow cytometry measures these particles as they pass by in a narrow flow. FIG. 4 shows the optical system of the white blood cell detection unit 41. In the same drawing, the beam emitted from a laser diode 401 irradiates, via a collimator lens 402, the blood cells passing through the interior of a sheath flow cell 403. The intensity of the front scattered light, the intensity of the side scattered light, and the intensity of the side fluorescent light from the blood cells within the sheath flow cell irradiated by the light are detected by the white blood cell detection unit 41.

The scattered light is a phenomenon due to the change in the direction of travel of the light caused by particles such as blood cells and the like which are present as obstructions in the direction of travel of the light. Information on the characteristics of the particles related to the size and composition of the particles can be obtained by detecting this scattered light. The front scattered light emerges from the particles in approximately the same direction as the direction of travel of the irradiating light. Characteristic information related to the size of the particle (blood cell) can be obtained from the front scattered light. The side scattered light emerges from the particle in an approximate perpendicular direction relative to the direction of travel of the irradiating light. Characteristic information related to the interior of the particle can be obtained from the side scattered light. When a particle is irradiated by laser light, the side scattered light intensity is dependent on the complexity (that is, nucleus shape, size, density, and granularity) of the interior of the cell. therefore, the blood cells can be classified (discriminated) and the number of cells can be counted by using the characteristics of the side scattered light intensity. Although the front scattered light and side scattered light are described as the scattered light used in the present embodiment, the present invention is not limited to this configuration inasmuch as scattered light of any angle may also be used relative to the optical axis of the light emitted from a light source that passes through the sheath flow cell insofar as scattered light signals are obtained which represent the characteristics of the particles necessary for analysis.

When fluorescent material such as a stained blood cell is irradiated by light, light is given off by the particle at a wavelength which is longer than the wavelength of the irradiating light. The intensity of the fluorescent light is increased by the stain, and characteristics information can be obtained relating to the degree of staining of the blood cell by measuring the fluorescent light intensity. The classification and other measurements of the white blood cells can then be performed by the difference in the (side) fluorescent light intensity.

As shown in FIG. 4, the front scattered light from the blood cell (white blood cells and nucleated red blood cells) which pass through the sheath flow cell 403 is received by a photodiode (front scattered light receiving unit) 406 through a collective lens 404 and pinhole 405. The side scattered light is received by a photo multiplexer (side scattered light receiving unit) 411 through a collective lens 407, dichroic mirror 408, optical filter 409, and pinhole 410. The side fluorescent light is received by a photo multiplexer (side fluorescent light receiving unit) 412 through the collective lens 407 and dichroic mirror 408. The photoreception signals output from the light receiving units 406, 411, and 412 are subjected to analog processing such as amplification and waveform processing and the like by an analog processing unit 5 which is configured by amps 51, 52, 53 and the like, and the analog-processed photoreception signals are provided to the microcomputer 6.

Figure 5:
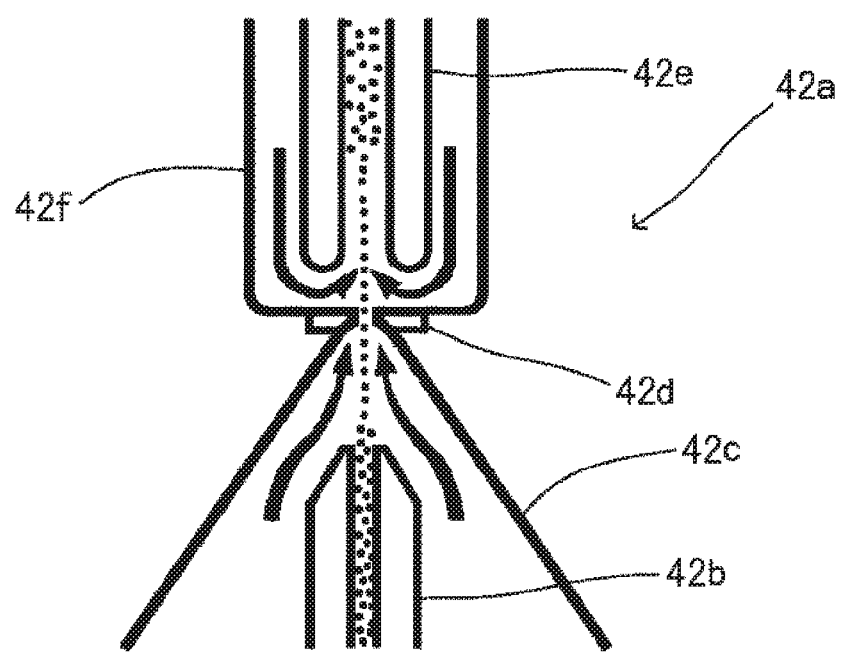
FIG. 5 shows the RBC/PLT detection unit.

The configuration of the RBC/PLT detection unit 42 is described below. FIG. 5 is a schematic view briefly showing the structure of the RBC/PLT detection unit 42. The RBC/PLT detection unit 42 is capable of measuring the numbers of red blood cells and platelets by a sheath flow-DC detection method. The RBC/PLT detection unit 42 has a sheath flow cell 42*a* as shown in FIG. 5. The sheath flow cell 42*a* is provided with a sample nozzle 42*b* which is open toward the top so that sample can be supplied from the reaction chamber 17 to the sample nozzle 42*b*. The sheath flow cell 42*a* has a tapered chamber 42*c* which narrows toward the top, and the sample nozzle 42*b* is disposed in the center part within the chamber 42*c*. An aperture 42*d* is provided at the top end of the chamber 42*c*, and this aperture 42*d* is aligned with the center position of the sample nozzle 42*b*. Measurement sample supplied from the sample supplying unit is sent upward from the tip of the sample nozzle 42*b*, and front sheath fluid is simultaneously supplied to the chamber 42*c* and flows upward toward the aperture 42*d*. The flow of the measurement sample, which is encapsulated in the front sheath fluid, is narrowly constricted by the tapered chamber 42*c* and the blood cells within the measurement sample pass one by one through the aperture 42*d*. Electrodes are provided at the aperture 42*d*, and a direct current is supplied between these electrodes. The change in the resistance of the direct current is detected at the aperture 42*d* when the measurement sample flows through the aperture 42*d*, and the electrical signal of the change in resistance is output to the controller 25. Since the resistance of the direct current increases when blood cells pass through the aperture 42*d*, the electrical signals reflect information of the passage of the blood cells through the aperture 42*d* so that the numbers of red blood cells and platelets can be counted by subjecting these electrical signals to signal processing.

A recovery tube 42*e*, which extends vertically, is provided above the aperture 42*d*. The recovery tube 42*e* is disposed within a chamber 42*f* which is connected to the chamber 42*c* through the aperture 42*d*. The inner wall of the chamber 42*f* is separated from the bottom end of the recovery tube 42*e*. The chamber 42*f* is configured to supply a back sheath, and this back sheath flows downward through the chamber 42*f* in a region outside the recovery tube 42*e*. The back sheath which flows outside the recovery tube 42*e* arrives at the bottom part of the chamber 42*f*, and thereafter flows between the inner wall of the chamber 42*f* and the bottom end of the recovery tube 42*e* so as to flow into the interior of the recovery tube 42*e*. The blood cells which has passed through the aperture 42*d* are therefore prevented from refluxing, thus preventing erroneous detection of the blood cells.

Figure 6:
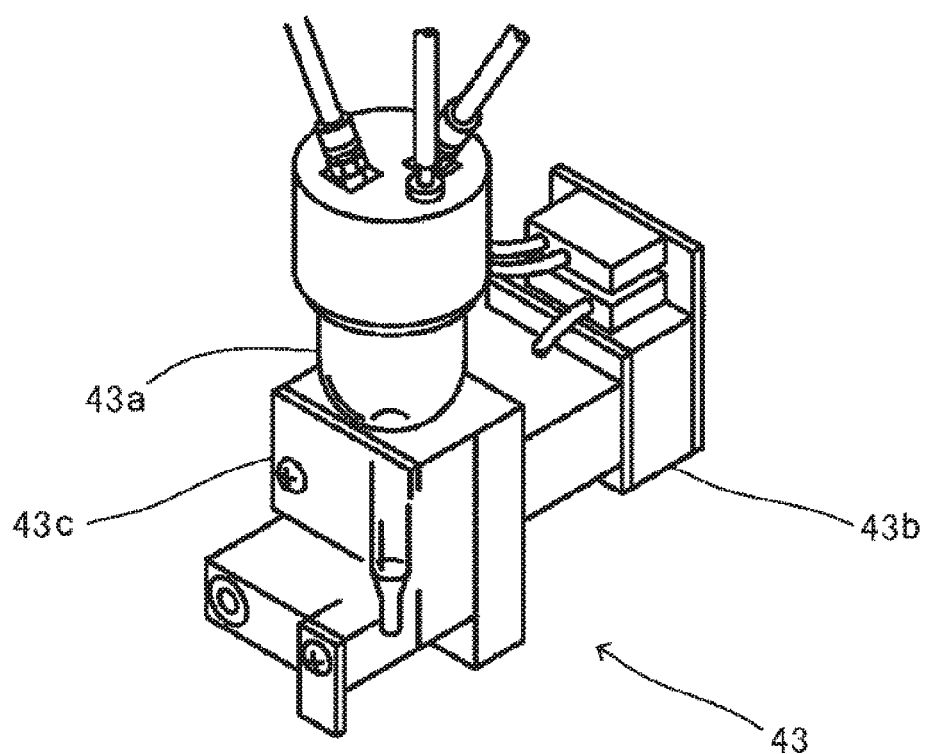
FIG. 6 shows the HGB detection unit.

The configuration of the HGB detection unit 43 is described below. The HGB detection unit 43 is capable of measuring the amount of hemoglobin (HGB) by an SLS hemoglobin method. FIG. 6 is a perspective view of the structure of the HGB detection unit 43. The HGB detection unit 43 has a cell 43*a* for accommodating a diluted sample, a light-emitting diode 43*b* for emitting light toward the cell 43*a*, and a photoreceptor element 43*c* for receiving the transmission light that has passed through the cell 43*a*. A fixed amount of blood is diluted with dilution fluid and a predetermined hemolytic agent at a predetermined dilution ratio by the sampling valve 12 to prepare a dilute sample. The hemolytic agent has properties which transform the hemoglobin in the blood to SLS-hemoglobin. The dilute sample is supplied to the cell 43*a* and accommodated therein. In this condition, the light-emitting diode 43*b* emits light that passes through the cell 43*a* and is received by the photoreceptor element 43*c* which is disposed opposite the light-emitting diode 43*b* with the cell 43*a* interposed therebetween. Since the light-emitting diode 43*b* emits light having a wavelength that is highly absorbed by the SLS-hemoglobin, and the cell 43*a* is configured of plastic material which has a high light transmittancy, the photoreceptor element 43*c* only receives the transmission light absorbed by the dilute sample of the light emitted from the light-emitting diode 43*b*. The photoreceptor element 43*c* outputs electrical signals which correspond to the amount of received light (optical density) to the microcomputer 6, and the microcomputer 6 compares the optical density with the optical density of the dilution solution which was measured previously, then calculates the hemoglobin value.

The microcomputer 6 is provided with an A/D converter 61 for converting the analog signals received from the analog processing unit 5 to digital signals. The output of the A/D converter 61 is sent to a calculation unit 62 of the microcomputer 6, and calculations are performed for predetermined processing of the photoreception signals in the calculation unit 62. The calculation unit 62 prepares distribution data (two-dimensional scattergrams (unclassified) and unidimensional histograms) based on the output of the detection device 4.

The microcomputer 6 is provided with a controller 63 configured by a memory for the control processor and the operation of the control processor, and a data analyzing unit 64 configured by a memory for the analysis processor and the operation of the analysis processor. The controller 63 controls the device 8 configured by a sampler (not shown in the drawing) for automatically supplying blood collection tubes, and a fluid system and the like for preparing and measuring samples, as well as performing other controls. The data analyzing unit 64 executes analysis processing such as clustering and the like on the distribution data. The analysis results are sent to an external data processing device 3 through an interface 65, and the data processing device 3 processes the data for screen display, storage and the like.

The microcomputer 6 is further provided with an interface 66 which is interposed between the microcomputer 6 and the display and operating unit 7, and an interface 67 which is interposed between the microcomputer 6 and the device 8. The calculation unit 62, controller 63, and interfaces 66 and 67 are connected through a bus 68, and the controller 63 and the data analyzing unit 64 are connected through a bus 69. The display and operating unit 7 includes a start switch by which the operator specifies to start a measurement, and a touch panel type liquid crystal display for displaying various types of setting values and analysis results, and receiving input from the operator.

Figure 7:
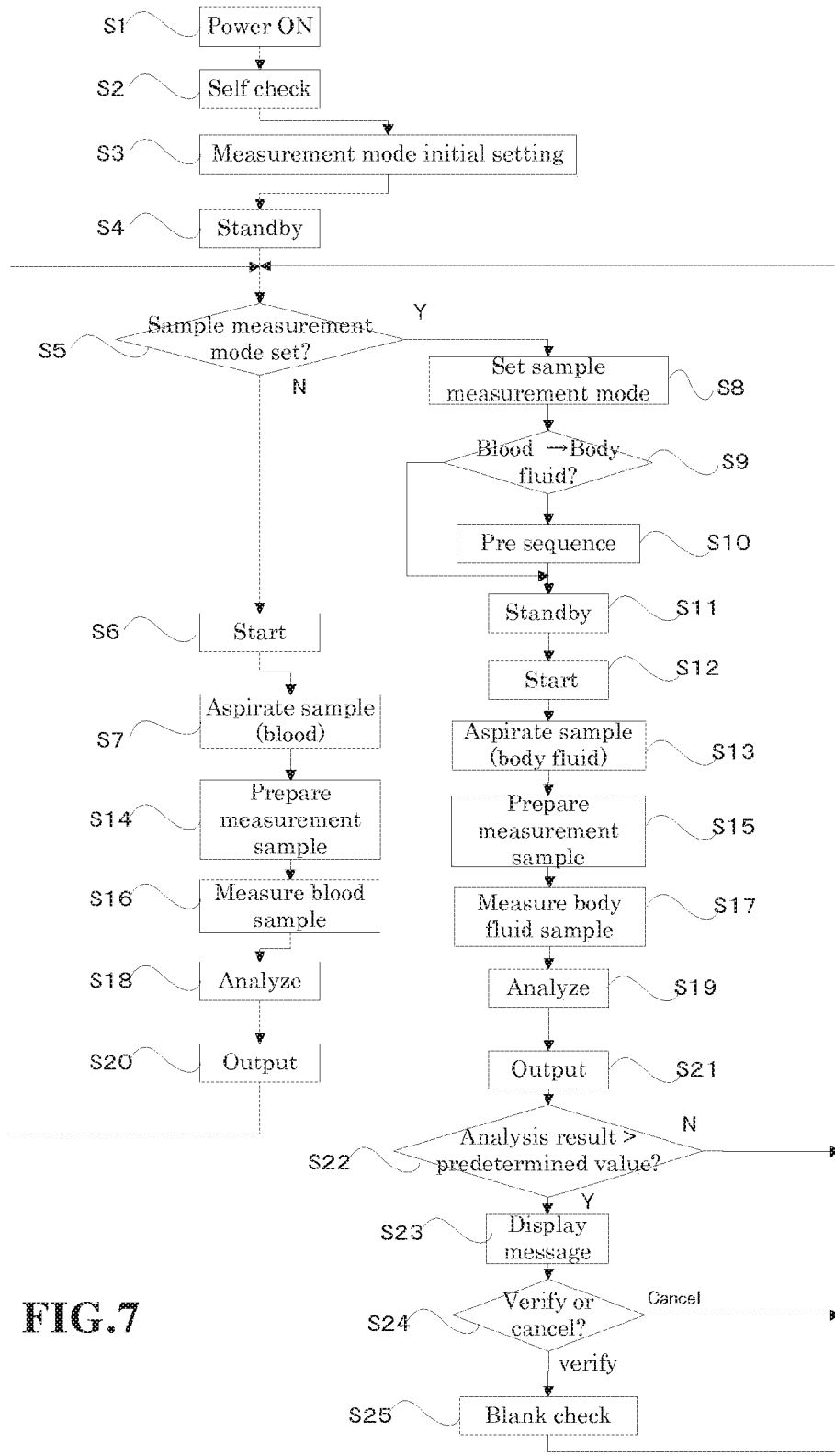
FIG. 7 is a flow chart of the sample measuring process.

The operation of the sample analyzer 1 of the present embodiment is described below. FIG. 7 is a flow chart showing the flow of the operation of the sample analyzer of the present embodiment. The sample analyzer 1 starts when a user turns on the power source of the sample analyzer 1 (step S1). The sample analyzer 1 first executes a self check during startup (step S2). In the self check, the microcomputer 6 tests and checks the operation of all operating device of the sample analyzer 1, and performs a blank check operation which measures a blank sample that does not contain a real sample. Next, the microcomputer 6 sets an initial measurement mode (step S3). The CBC+DIFF mode is the initial setting. Specifically, in the process of step S3, parameters (operating conditions) for performing blood measurements are set, for example, which reaction chamber to use and the set time for the measurement. The blood measurement mode is thus set as the initial operating mode in the sample analyzer 1 of the present embodiment. The sample analyzer 1 therefore remains in a standby state waiting to receive a measurement start instruction. The microcomputer 6 displays a screen on the liquid crystal display which alerts the operator to the standby state (step S4).

In the standby state, the operator can change the measurement mode by operating the display and operation unit 7. FIG. 8 is a schematic view of an input screen for setting the measurement mode. This screen is provided with discrete display regions including the sample number 120, type of sample uptake mode 121, type of discrete test (measurement mode) 122, and type of sample 123. The three sample uptake modes include a manual mode for aspirating a sample after the operator has manually inserted a sample container in the sample aspiration nozzle 18, a capillary mode for aspirating a measurement sample via the sample aspiration nozzle 18 after the operator has previously prepared the measurement sample by mixing a sample and reagent, and a closed mode for supplying a sample by automatically transporting a sample container using a conveyer device. The types of samples include NORMAL, which are normal blood samples; HPC, which are hematopoietic progenitor cell samples; and BODY FLUID, which are other fluids of the body. The operator can specify the sample take-up mode, measurement mode, and type of sample. When the blood measurement mode has been specified, the NORMAL sample type is specified, and an optional sample take-up mode and measurement mode are specified. When specifying the BODY FLUID measurement mode, the operator specifies MANUAL mode as the take-up mode, [CBC+DIFF], [CBC+DIFF+RET], [CBC+DIFF+NRBC], or [CBC+DIFFNRBC+RET] as the DISCRETE test, and [BODY FLUID] as the type of sample. In step S4, the operator specifies the desired mode. The operator presses the start switch to start the measurement when blood measurement is performed without changing the initially set measurement mode (step S5: N). The microcomputer 6 receives the instruction to start the measurement (step S6), and the blood sample is aspirated by the sample aspiration nozzle (step S7).

After the blood sample has been aspirated, the sample is introduced to the previously mentioned sampling valve 18, and the necessary sample preparation is performed for the measurement according to the type discrete test of the measurement mode (step S14). The measurement operation is then executed for this measurement sample (step S16). When [7] is set as the type of discrete test, for example, HGB, WBC/BASO, DIFF, RET, NRBC, and RBC/PLT measurement samples are prepared. Thereafter, the WBC/BASO, DIFF, RET, and NRBC measurement samples are measured by the white blood cell detection unit 41, the RBC/PLT measurement sample is measured by the RBC/PLT detection unit 42, and the HGB measurement sample is measured by the HGB detection unit 43. At this time, the WBC/BASO, DIFF, RET, and NRBC measurement samples are introduced to the white blood cell detection unit 41 in the order NRBC, WBC/BASO, DIFF, RET and sequentially measured since only a single white blood cell detection unit 41 is provided. In this measurement operation, the calculation unit 62 creates particle distribution maps (scattergram, histogram). The scattergram created from the optical information obtained by the DIFF measurement is described below. The calculation unit 62 generates a two-dimensional scattergram (particle distribution map) using, as characteristic parameters, the side scattered light and side fluorescent light among the photoreception signals output from the white blood cell detection unit 41 in the DIFF measurement. This scattergram (referred to as "DIFF scattergram" hereinafter) plots the side scattered light intensity on the X axis and the side fluorescent light on the Y axis; red blood cell ghost clusters, lymphocyte clusters, monocyte clusters, neutrophil+basophil clusters, and eosinophil clusters normally appear. These clusters are recognized by processing performed on the DIFF scattergram by the data analyzing unit 64.

Figure 12:
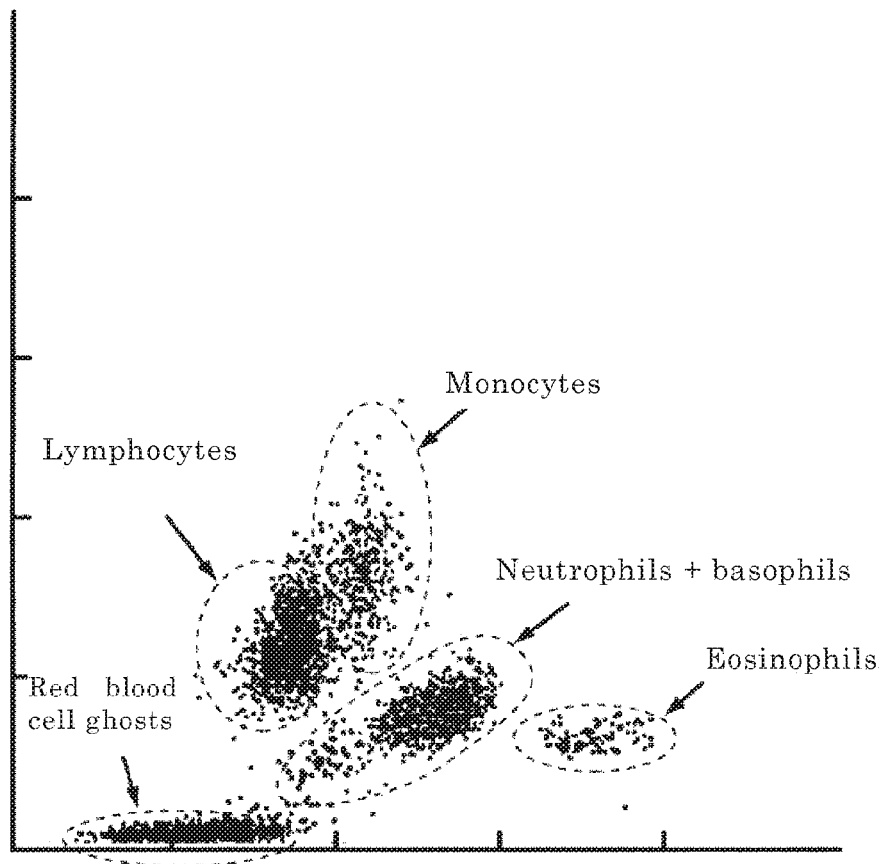
FIG. 12 is a schematic view of a scattergram derived from measurements of a DIFF measurement sample prepared from blood.

Analysis processing is then performed based on the particle distribution maps obtained by the measurement (step S18). In the analysis processing, the data analyzing unit 64 of the microcomputer 6 classifies the four white blood cell clusters (lymphocyte cluster, monocyte cluster, neutrophil+basophil cluster, and eosinophil cluster), and the red blood cell ghost cluster as shown in FIG. 12 from the DIFF scattergram prepared by the calculation unit 62 when the DIFF measurement samples were measured by the white blood cell detection unit 41. In the analysis process of the present embodiment, each particle plotted on the scattergram and the degree of attribution of particles to each cluster at a distance from the center of gravity of each cluster is obtained. Then, each particle is attributed to a cluster according to the degree of attribution. The particle classification method is disclosed in detail in U.S. Pat. No. 5,555,196. The basophil cluster, and white blood cell clusters other than basophils, and the red blood cell ghost cluster are classified on the scattergram obtained by the WBC/BASO measurement. White blood cells are classified in five groups based on the results of the four classifications and numbers of white blood cells (refer to FIG. 12) by the analysis processing of the DIFF scattergram, and the results of the two classification and numbers of white blood cells by the analysis processing of the WBC/BASO scattergram. Specifically, the data analysis unit 64 subtracts the basophil cell count obtained by the analyzing the WBC/BASO scattergram from the neutrophil+basophil cell count obtained by analyzing the DIFF scattergram, to obtain the neutrophil cell count and the basophil cell count. Thus, five classifications of white blood cells are obtained as well as the number of blood cells in each classification. In addition, the trough is detected in the curve in the unidimensional histogram created based on the characteristic information from the detection unit 42, and the particles are classified as red blood cells and platelets in the RBC/PLT measurement. The analysis results thus obtained are output to the display unit 302 of the data processing unit 3 (step S20).

When input specifying the measurement mode is received as described above in step S5, the microcomputer 6 sets the parameters (operating conditions) for the body fluid measurement, for example, the reaction chamber to use and the set time of the measurement and the like (step S8). In the present embodiment, the measurement time is three times the time for blood measurement, as will be described later.

The measuring unit 2 starts the pre sequence (step S10) when the measurement mode has been switched from the previous measurement mode (in this instance, the blood measurement mode) to the body fluid measurement mode (step S9). The pre sequence is a process of preparing for the body fluid measurement. Since samples which have a low concentration of blood cell component are measured in the body fluid measurement, the setting is switched from the blood measurement mode ([1:NORMAL] is displayed in FIG. 8) to the body fluid measurement mode, and the lack of background influence is confirmed in the body fluid measurement results.

The pre sequence includes a blank check operation. The blank check determination standard of the pre sequence is set at a fraction and is more strict than the determination standard of the blank check (for example, the blank check performed after power on and automatic wash) performed in the blood measurement mode. When the setting is changed from the body fluid measurement mode to the blood measurement mode, this pre sequence is not performed since there is no background influence (carry over effect) on the normal blood measurement results. Furthermore, when body fluid samples are measured in a repeated body fluid measurement mode, this pre sequence is not performed since there is normally no background influence. There is concern, however, that the next sample measurement may be affected when the body fluid sample analysis results exceed a predetermined value, due to an extremely high number of particles in the body fluid since the measurement results are high, and therefore the operator is alerted of this concern that the analysis results of the next sample may be affected. Then, the blank check measurement is performed. A configuration is desirable in which a message "please press VERIFY" is output to the screen, and the blank check is performed when the operator presses the VERIFY button. In this case, a configuration is possible in which a CANCEL button may be provided on the screen to transition to the standby screen without performing a blank check when the operator presses the CANCEL button. It is also desirable that a flag indicate the low reliability of the measurement results when a blank check is not performed. Wasted reagent and time can thus be avoided by performing an additional blank check only when needed.

Figure 9:
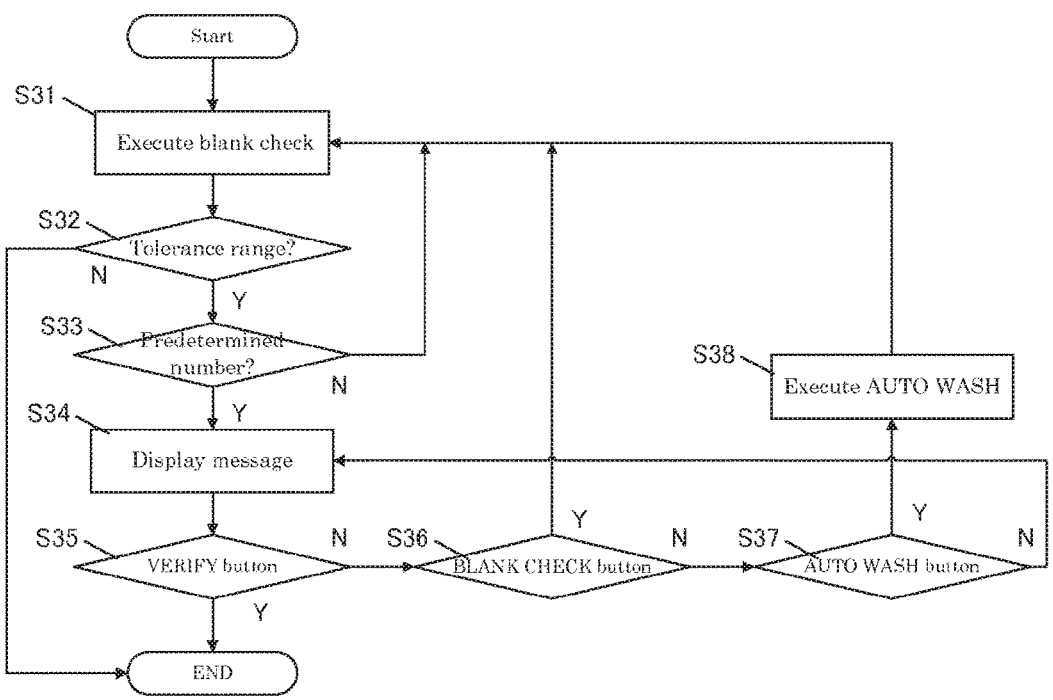
FIG. 9 is a flow chart showing the pre sequence process.

FIG. 9 is a flow chart showing the sequence of the pre sequence process performed when the measurement mode is changed from the blood measurement mode to the body fluid measurement mode. The sample analyzer 1 performs the pre sequence by measuring a blank sample using the measuring unit 2 (step S31), comparing the measurement result with predetermined tolerance values and determining whether or not the measurement results are less than the tolerance values using the microcomputer 6 (step S32). When the measurement results are less than the tolerance values, the microcomputer 6 ends the pre sequence and the process returns. When the measurement results are not less than the tolerance value, the microcomputer 6 determines whether or not the blank check was executed the set number of times (for example, three times) (step S33), and when the number of executions of the blank check is less than a predetermined number, the process returns to step S31 and the blank check is performed again for the predetermined number of times. When the measurement results of the blank check performed a predetermined number of times are not less than the tolerance values, a screen is displayed with includes a VERIFY button, BLANK CHECK button, and AUTOMATIC WASH button and the blank check measurement results are displayed on the display and operation unit 7 (step S34). When the operator has pressed the VERIFY button (step S35), the microcomputer 6 ends the pre sequence and the process returns. When the BLANK CHECK button has been pressed (step S36), the process returns to step S31 and the blank check is performed again; when the AUTOMATIC WASH button has been pressed (step S37), automatic washing is performed using a special washing solution (step S38), and thereafter the process returns to step S31 and the blank check is performed again.

When the pre sequence ends as described above, the sample analyzer 1 enters the standby state (step S11). When the operator presses the start switch and starts the body fluid measurement, the sample aspiration nozzle 18 of the measuring unit 2 is immersed in the sample container in the same manner as for the manual measurement of the blood sample. When the instruction to start measurement is received by the microcomputer 6 (step S12), the body fluid aspiration begins (step S13).

After the body fluid sample has been aspirated, the body fluid sample is introduced to the sampling valve 91 in the same manner as the blood sample. Then, the RBC/PLT measurement sample is prepared by the reaction chamber 13 (step S15). Subsequently, the DIFF measurement sample is measured by the white blood cell detection unit 41, and the RBC/PLT measurement sample is measured by the RBC/PLT detection unit 42 (step S17). Since only the DIFF measurement sample is measured by the white blood cell detection unit 41 in the body fluid measurement mode, the measurement is completed in a shorter time than the blood measurement even though the measurement time is longer than the measurement time in the blood measurement mode. The analysis accuracy of the low particle concentration body fluid sample can therefore be improved by increasing the measurement time of the body fluid measurement to be longer than the measurement time of the blood measurement. Although the measurement accuracy can be improved due to the increased number of particles counted by lengthening the measurement time, a two to six fold increase in the measurement time is suitable because the sample processing ability is reduced when the measurement time is excessively long, and there is a limit to the performance of the syringe pump which delivers the measurement sample to the white blood cell detection unit 41. In the present embodiment, the measurement time in the body fluid measurement mode is set at three times the measurement time of the blood measurement mode.

The RBC/PLT measurement sample is introduced to the electrical resistance detection unit 41 in the same manner for all measurement modes, and measurement is performed under a fixed flow speed condition. The analysis processing is performed thereafter based on the characteristic information obtained by the measurements (step S19), and the analysis results are output to the display unit 302 of the data processing unit 3 (step S21). In the analysis processing of the blood measurement mode, the DIFF scattergram and the like are analyzed, and information is calculated for five types of white blood cell subclasses (NEUT: neutrophil, LYMPH: lymphocyte, MONO: monocyte, EO: eosinophil, and BASO: basophil), whereas in the analysis processing of the body fluid measurement mode, two subclasses (MN: mononuclear cell, PMN: polymorphonuclear cell) are classified in a partially integrated form because there are a lesser number of blood cells and these cells are sometimes damaged. The lymphocytes and monocytes belong to mononuclear cells, and neutrophils, eosinophils, and basophils belong to polymorphonuclear cells. Since the classification algorithm is the same as the algorithm described for the analysis processing in the blood measurement mode, further description is omitted.

Figure 17:
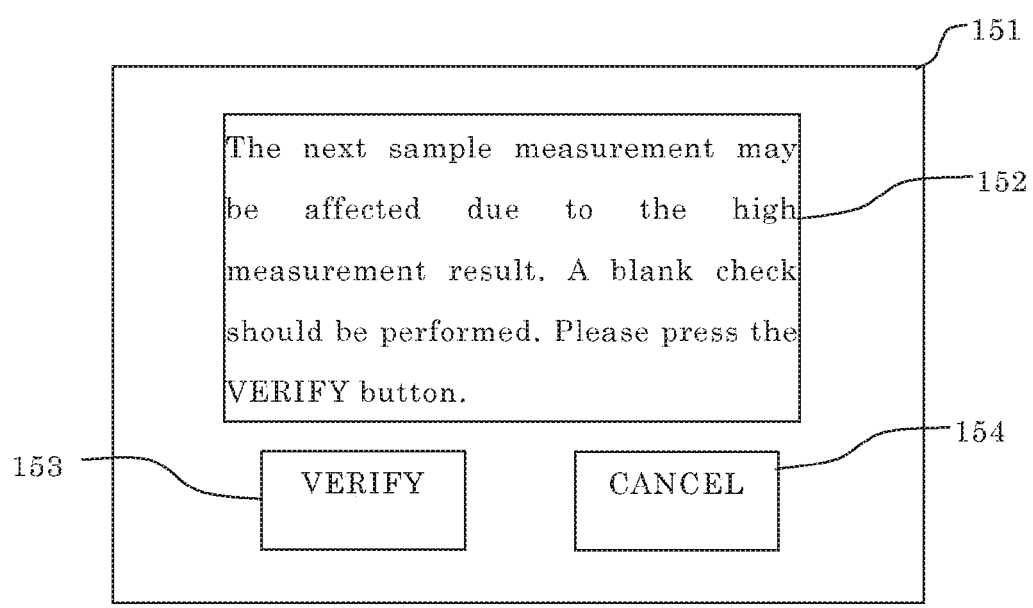
FIG. 17 is a confirmation screen at the start of the blank check which is displayed in the body fluid measurement mode.

Next, the analysis results obtained in step S19 are compared to the tolerance value (predetermined threshold value) (step S22). The tolerance value is the same value as the tolerance value used in the blank check of the pre sequence performed in step S10. When the analysis result is greater than the tolerance value (step S22: Y), the verification screen 151 at the start of the blank check is displayed, as shown in FIG. 17. A message is displayed on the verification screen 151 indicating there is concern that the measurement of the next sample may be influenced due to the high measurement result. Then, the blank check measurement is performed. A message display area 152 for displaying the message "please press the VERIFY button", a VERIFY button 153, and a CANCEL button 154 are displayed. Next, determinations are made as to whether or not the user has pressed the VERIFY button 153 or the CANCEL button 154 (step S24), and the blank check is executed when the VERIFY button has been pressed (VERIFY in step S24) (step S25). The process returns to step S5 without performing the blank check when the analysis result obtained in step S19 is less than the tolerance value (step S22: N), and the when the CANCEL button has been pressed (CANCEL in step S24).

Anomalous particles (macrophages, mesothelial cells, tumor cells and the like) other than blond cells may be present in the body fluid sample. Although it is rare for such anomalous cells to be present in cerebrospinal fluid, such cells appear comparatively frequently in abdominal and thoracic fluids. The influence of these anomalous particles must be eliminated in order to obtain a high precision classification of blood cells within the body fluid regardless of the type of body fluid. White blood cells in body fluid can be measured with greater precision based on the new knowledge than anomalous particles appear in the top part of the DIFF scattergram produced by this blood cell analyzer of the present invention. This aspect was not considered in the previously mentioned conventional art.

Figure 10:
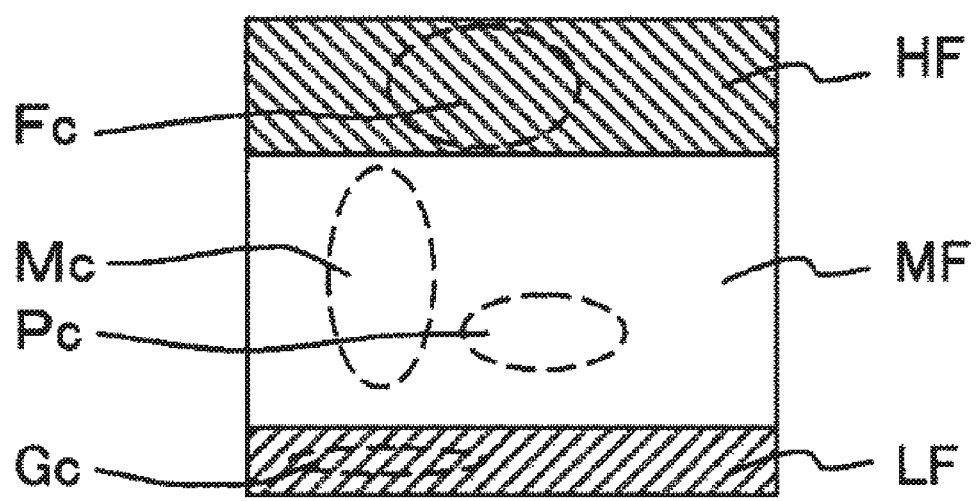
FIG. 10 is a schematic view of a scattergram derived from measurements of a DIFF measurement sample prepared from body fluid.

FIG. 10 is a schematic view of a scattergram obtained by measuring and analyzing a DIFF measurement sample prepared from body fluid and white blood cell measurement reagent in the body fluid measurement mode of the blood cell analyzer 1 of the present embodiment. The vertical axis of the scattergram represents the side fluorescent light intensity (the fluorescent light intensity at the top is greatest), and the horizontal axis represents the side scattered light intensity (the scattered light intensity at the right side is greatest). A red blood cell ghost Gc caused by hemolysis is distributed in the region LF in which the fluorescent light intensity is weakest in the scattergram, anomalous particles such as mesothelial cells and the like is distributed in the region HF in which the fluorescent light intensity is greatest, and mononuclear white blood cells Mc and polynuclear white blood cells Pc are distributed in the intermediate region MF. In the analysis of the scattergram, the particle component distributed in the region MF is analyzed as white blood cells after excluding region LF and region HF, and the particles are classified and counted in two groups. Lymphocytes and monocytes are included in the mononuclear white blood cells Mc, and neutrophils, basophils, and eosinophils are included in the polynuclear white blood cells Pc.

Since fewer and damaged blood cells are contained in body fluid, white blood cells are classified and counted as mononuclear white blood cells and polynuclear white blood cells when analyzing white blood cells in body fluid.

Anomalous particles (nucleated cells such as tumor cells, macrophages, mesothelial cells) other than blood cells may also be present in body fluid. Although it is rare for such anomalous cells to be present in cerebrospinal fluid, such cells appear comparatively frequently in abdominal and thoracic fluids. In the scattergram of FIG. 10, such nucleated cells other than white blood cells are distributed in region HF. In the present embodiment, it is possible to determine accurate white blood cells counts even in body fluid which contains such nucleated cells other than white blood cells since nucleated cells other than white blood cells can be identified. The degree of occurrence of anomalous cells can be determined by counting the cells which appear in region HF. In the present embodiment, cells are demarcated in the regions LF, MF, and HF by threshold values for demarcating each region; these threshold values may also be changed manually.

FIG. 11 compares the analysis results of the blood cell analyzer 1 of the present embodiment and the count results of a reference method to show the validity of the scattergram analysis method described above. The sample material is thoracic fluid; in the drawing, "this method" refers to the white blood cell count (WBC) and anomalous particle count (Others) calculated by the blood cell analyzer 1 of the present embodiment, and "Ref" refers to the calculation result by the reference methods (Fuchs Rosenthal calculation method and site-spin method). Examples 1, 2, and 3 are the results of analysis of thoracic fluid in which anomalous particles were plentiful, and the correlation between the reference methods and the analysis results of the blood cell analyzer 1 of the present invention can be readily understood.

Figure 13:
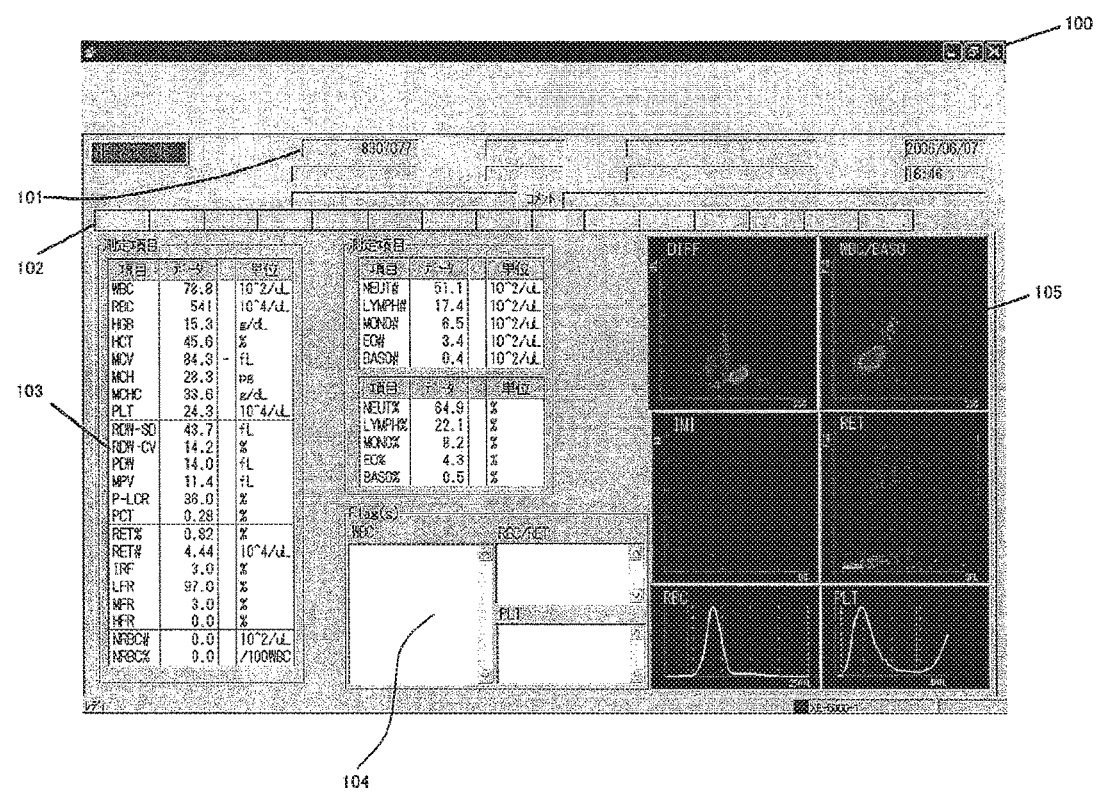
FIG. 13 is a display screen showing the measurement results in the blood measurement mode.

FIG. 13 shows a screen 200 which is displayed on the display unit 302 of the data processing unit 3, showing the analysis results of the DIFF measurement sample prepared from blood. A sample number display region which displays a sample number 101 is provided at the top of the screen 200, and an attribute display region which displays patient attributes is provided adjacently. The attribute display region specifically includes a patient ID, patient name, date of birth, sex, hospital department/ward, attending physician, date of measurement, time of measurement, comments and the like. A measurement result display region which displays the measurement results is provided at the bottom of the attribute display region. The measurement result display region includes several pages, and these pages can be displayed by selecting a plurality of tabs 102. Tabs have a plurality of arrangements matching the main screen, graph screen, and measurement items. FIG. 12 is a screen which is displayed when the graph screen tab has been selected. A graph display region 104 for displaying graphs and a measurement value display region 103 for displaying the measurement result values are provided in the left half of the measurement value display region, and a distribution map display region for displaying the measurement result distribution map 105 is provided in the right half. WBC, RBC, NEUT#, . . . , BASO#, . . . , NEUT#, . . . , BASO % and the like, data, and units are displayed in the measurement value display region, and flagging results representing sample anomalies and disease suspicions which are clinically useful information relating to WBC, PLT, RBC or RET are displayed in the flag display region 104.

Six distribution maps are displayed in the distribution map display region 105. The scattergram on the upper left side is a DIFF scattergram. The WBC/BASO scattergram is shown at the top right, the immature cell (IMI) scattergram is shown at mid left, and the RET scattergram is shown at mid right. The RBC scattergram is shown at the bottom left, and the PLT scattergram is shown at the bottom right.

Figure 14:
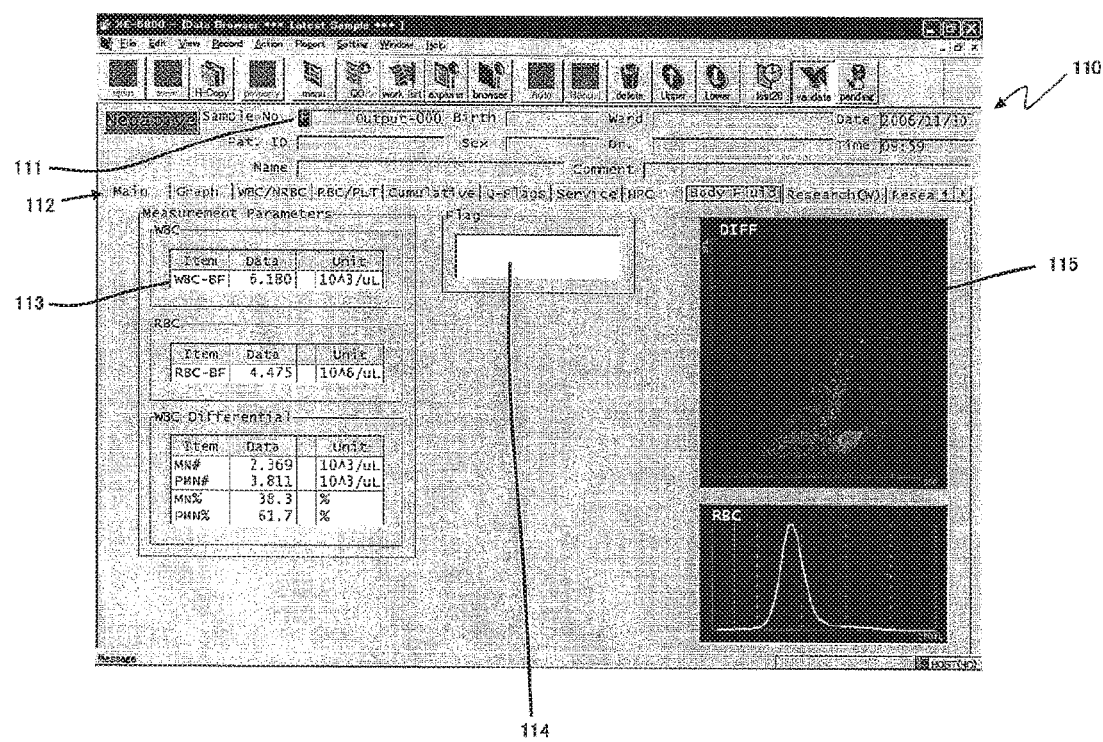
FIG. 14 is a display screen showing the measurement results in the body fluid measurement mode.

FIG. 14 shows a screen 110 displayed in the display area 302 of the data processing unit 3 as the measurement results of the DIFF measurement sample prepared from body fluid. A sample number display region 111 for displaying a sample number is provided at the top of the screen 110, and a patient attribute display region is provided adjacently. An [F], which indicates measurement has been conducted in the body fluid measurement mode, is displayed at the left end of the sample number display region 111. Thus, it can be clearly recognized that the analysis results are for body fluid measurement results. The measurement result display region includes a plurality of pages which are selectable by tab 112. In this example, the tab for body fluid measurement is selected.

The measurement value display region 113 includes the name of the measurement items for body fluid measurement rather than the measurement results of the blood measurement mode; WBC-BF (WBC count), RBC-BF (RBC count), MN# (mononuclear cell count (lymphocytes+monocytes)), PMN# (polymorphonuclear cell count (neutrophils+basophils+eosinophils)), MN % (ratio of mononuclear cells among white blood cells), PMN % (ratio of polymorphonuclear cells among white blood cells), measurement values, and units are associated and displayed. A flag display region 114 is provided in the body fluid measurement similar to the blood measurement. Two distribution maps 115 are displayed in the distribution map display region, and the top scattergram is a DIFF scattergram. The bottom scattergram is an RBC scattergram.

Figure 15:
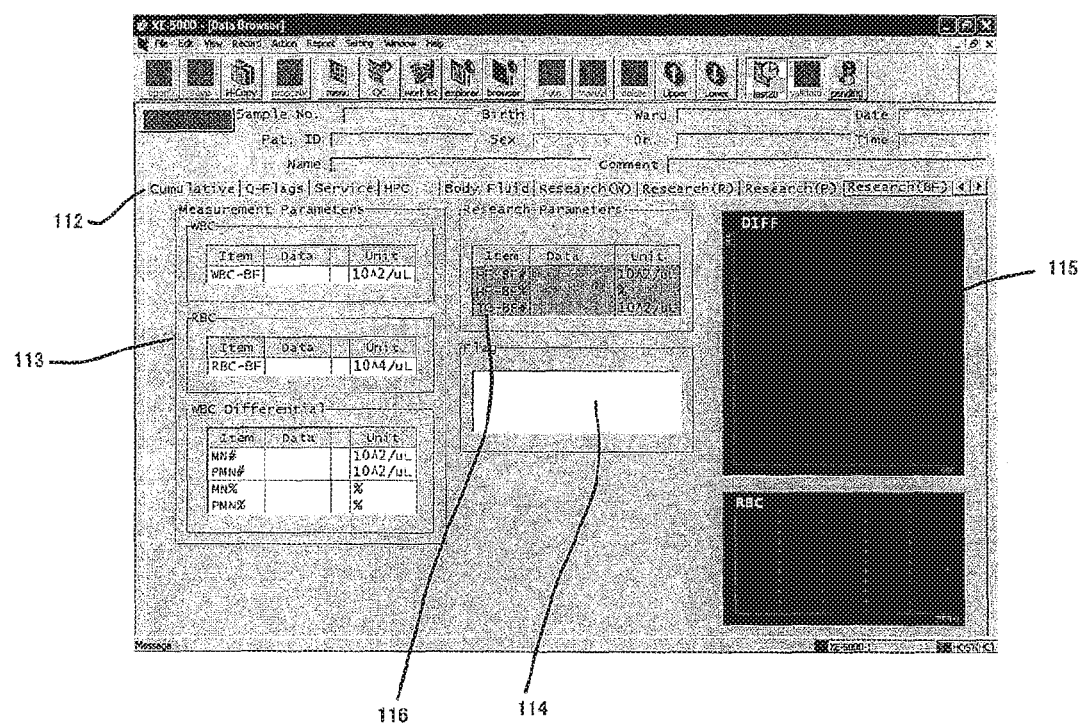
FIG. 15 is a display screen showing the measurement results in the body fluid measurement mode.

FIG. 15 shows an example in which the Research BF tab 112 is selected in the screen 110 of FIG. 14. This screen displays the same items as screen 110 with the exception that a research parameter display region 116 is also displayed. The research parameter display region 116 displays number of particles in region HF [HF-BF#], the ratio of the number of particles in the region HF relative to the number of particles in the region including both region HF and region MF [HF-BF %], and the number of particles in the region including both region HF and region MF [TC-BF#] in FIG. 10. [HF-BF %] is the percentage of HF-BF relative to TC-BF.

Figure 16:
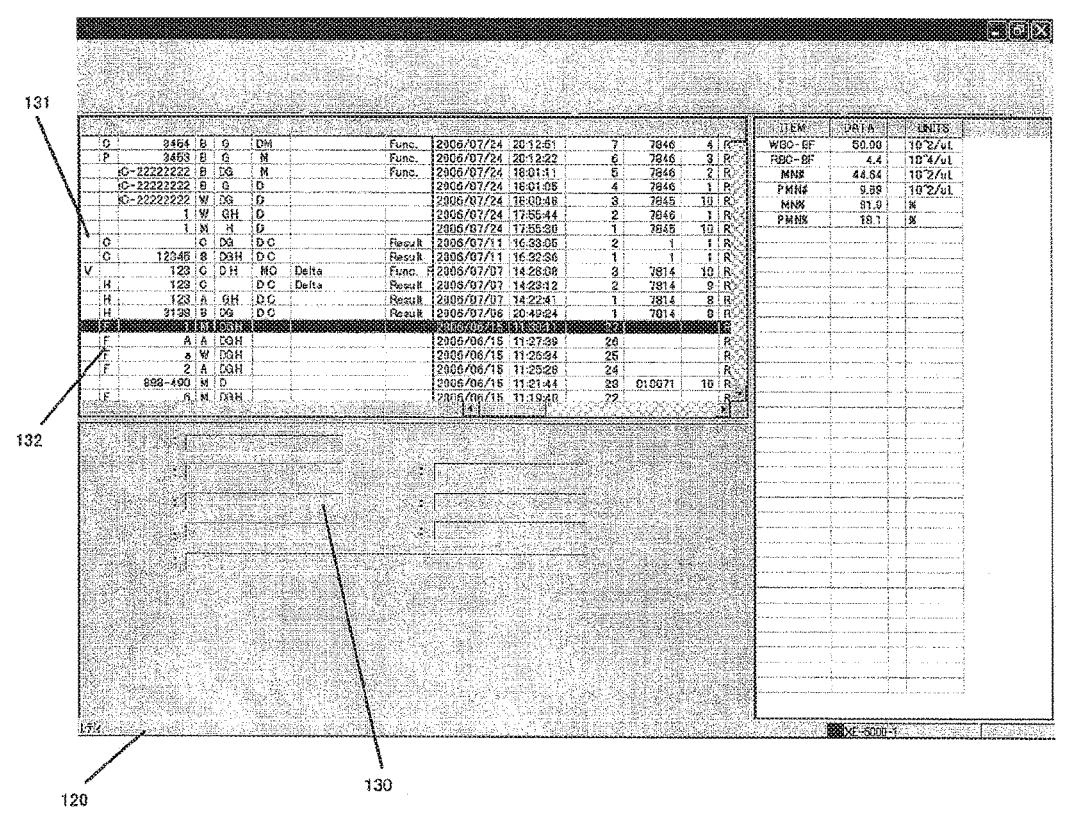

FIG. 16 shows a screen 120 showing a list of stored samples which is displayed on the display unit 302 of the data processing unit 3. Reference number 130 refers to a patient attribute display region. Provided above this region is a measurement result display region which displays the measurement result selected by a tab. A row 131 on the left end of the measurement result display region is used to indicate whether the validation operation has been performed or not for the measurement result. A "V" symbol indicates validation has been performed. A row 132 on the right indicates the measurement mode. An "F" symbol indicates the measurement results are for the body fluid mode. Although there are high value samples that require blank checking in the body fluid mode, and inverted "F" symbol can be displayed to indicate the blank check has not been performed (that is, CANCEL was selected in step S24).

Although the structure and functions of the blood cell analyzer of the present invention have been described as being pre-established in the blood cell analyzer, the same functions may be realized by a computer program so that the functions of the present invention can be realized in a conventional blood cell analyzer by installing the computer program in a conventional blood cell analyzer.

Although the amount of sample, type of reagent, and amount of reagent are the same when preparing measurement samples for the white blood cell classification measurement in the blood measurement mode and the white blood cell classification measurement in the body fluid measurement mode in the present embodiment, the present invention is not limited to this configuration inasmuch as the amount of sample and the amount of reagent used to prepare a measurement sample for white blood cell classification in the body fluid measurement mode may be greater than the amount of sample and the amount of reagent used to prepare a measurement sample for white blood cell classification in the blood measurement mode. Since the measurement time is greater and the amount of measurement sample needed for measurement is greater for white blood cell classification in the body fluid measurement mode than in the blood measurement mode, it is thereby possible to prepare suitable amounts of measurement sample for white blood cell classification in the blood measurement mode and for white blood cell classification in the body fluid measurement mode. Moreover, the type of reagent used for white blood cell classification in the blood measurement mode may differ from the type of reagent used for white blood cell classification in the body fluid measurement mode.

Although white blood cell classification is performed in the body fluid measurement mode using scattered light and fluorescent light in the present embodiment, the present invention is not limited to this configuration inasmuch as white blood cell classification may also be performed in the body fluid measurement mode using, for example, scattered light and absorbed light. The measurement of absorbed light may be accomplished by preparing a measurement sample by mixing a staining reagent to stain the white blood cells, and other reagent together with the sample, supplying this measurement sample to a flow cell to form a sample flow within the flow cell, irradiating this sample flow with light, and receiving the light emitted from the sample flow via a photoreceptor element such as a photodiode or the like. The light is absorbed by the white blood cells when the white blood cells pass through the flow cell, and the degree of that absorption can be grasped as the amount of light received by the photoreceptor element. Such measurement of absorbed light is disclosed in U.S. Pat. Nos. 5,122,453, and 5,138,181. Furthermore, electrical resistance may be measured rather than scattered light, in which case white blood cells can be classified by the electrical resistance and absorbed light.

What is claimed is:

1. A sample analyzer comprising:
a plurality of detectors each configured to sense cells in a sample, the sample selectively comprising (i) a blood sample or (ii) a body fluid sample, wherein the body fluid sample contains body fluid, other than blood, which is selected from a group consisting of cerebrospinal fluid, thoracic fluid, abdominal fluid, fluid collected in a cardiac sac, synovial fluid, dialysate from peritoneal dialysis, and intraperitoneal rinse;
a controller programmed to selectively operate the sample analyzer in a blood measuring mode or a body fluid measuring mode, wherein the blood measuring mode includes a sequence of operations for measuring cells in the blood sample, and the body fluid measuring mode includes a sequence of operations for measuring cells in the body fluid sample, wherein a respective sequence of operations for measuring cells in the blood sample and in the body fluid sample comprises (a) a sensing operation comprising operations of preparing for measurement and operating a detector to sense the cells in the sample and (b) an analyzing operation comprising operations of analyzing sample measurements and displaying analysis results, the sensing operation performed in the body fluid measuring mode being different, at least partially, from the sensing operation performed in the blood measuring mode, and further wherein the plurality of detectors includes one or more multi-mode detectors configured to operate in both the blood measuring mode and the body fluid measuring mode, the controller programmed to:
perform the sensing operation in the blood measuring mode to: introduce the blood sample into a multi-mode detector; operate said multi-mode detector to sense cells in the introduced blood sample; and derive blood-sample measurements of cells in the introduced blood sample; and
perform the sensing operation in the body fluid measuring mode to: introduce the body fluid sample into said multi-mode detector; operate said multi-mode detector to sense cells in the introduced body fluid sample; and derive body-fluid-sample measurements of cells in the introduced body fluid sample.

2. The sample analyzer according to claim 1, wherein
the sensing operation performed in the blood measuring mode comprises sensing the cells in the introduced blood sample for a first measurement time, and
the sensing operation performed in the body fluid measuring mode comprises sensing the cells in the introduced body fluid sample for a second measurement time, wherein the second measurement time is longer than the first measurement time according to a cell concentration of the sample.

3. The sample analyzer according to claim 1, wherein the sensing operation performed in the body fluid measuring mode comprises automatically initiating pre-washing said multi-mode detector to reduce a carryover effect on measurements of the cells in the body fluid sample, wherein the controller is programmed to automatically initiate said pre-washing before introducing the body fluid sample into said multi-mode detector during said sensing operation in the body fluid measuring mode.

4. The sample analyzer according to claim 3, wherein the operation of pre-washing said multi-mode detector is automatically initiated in the sensing operation in the body fluid measuring mode but not automatically initiated in the sensing operation in the blood measuring mode.

5. The sample analyzer according to claim 4, wherein the operation of automatically initiated pre-washing includes using solution different from solution for washing said multi-mode detector in the blood measuring mode.

6. The sample analyzer according to claim 5, wherein the operation of automatically initiated pre-washing includes using a solution specifically prepared for the operation of automatically initiated pre-washing.

7. The sample analyzer according to claim 1, wherein the analyzing operation performed in the body fluid measuring mode comprises operations of: analyzing the body-fluid-sample measurements; and counting a type of cells among the cells in the introduced body fluid sample based on the analyzed body-fluid-sample measurements.

8. The sample analyzer according to claim 7, wherein the sensing operation performed in the body fluid measuring mode comprises operations of counting mono-nucleated cells and poly-nucleated cells among the cells in the introduced body fluid sample and separately displaying in a screen a count of the mono-nucleated cells and a count of the poly-nucleated cells.

9. The sample analyzer according to claim 8, wherein the analyzing operations performed in the body fluid measuring mode comprises operations of calculating a relative amount of the mono-nucleated cells and a relative amount of the poly-nucleated cells and separately displaying in a screen the relative amount of the mono-nucleated cells and the relative amount of the poly-nucleated cells.

10. The sample analyzer according to claim 9, wherein the analyzing operation performed in the body fluid measuring mode comprises an operation of counting a total of nucleated cells.

11. The sample analyzer according to claim 1, wherein the controller is programmed to:
introduce a cell-free sample into said multi-mode detector, the cell-free sample having no cells contained in the cell-free sample; and
sense the cell-free sample by said multi-mode detector, and
the controller is further programmed to analyze measurements of the cell-free sample and count cells carried over into the cell-free sample from a test sample previously measured.

12. A sample analyzer comprising:
a plurality of detectors each configured to sense cells in a sample, the sample selectively comprising (i) a blood sample or (ii) a body fluid sample, wherein the body fluid sample contains body fluid, other than blood, which is selected from a group consisting of cerebrospinal fluid, thoracic fluid, abdominal fluid, fluid collected in a cardiac sac, synovial fluid, dialysate from peritoneal dialysis, and intraperitoneal rinse;
a controller programmed to selectively operate the sample analyzer in a blood measuring mode or a body fluid measuring mode, wherein the blood measuring mode includes a sequence of operations for measuring cells in the blood sample, and the body fluid measuring mode includes a sequence of operations for measuring cells in the body fluid sample, wherein a respective sequence of operations for measuring cells in the blood sample and in the body fluid sample comprises (a) a sensing operation comprising: operations of preparing for measurement and operating a detector to sense the cells in the sample and (b) an analyzing operation comprising operations of analyzing sample measurements and displaying analysis results, the sensing operation performed in the body fluid measuring mode being different, at least partially, from the sensing operation performed in the blood measuring mode, and further wherein the plurality of detectors includes one or more multi-mode detectors configured to operate in both the blood measuring mode and the body fluid measuring mode, the controller programmed to:
perform the sensing operation in the blood measuring mode to: introduce the blood sample into a multi-mode detector; operate said multi-mode detector to sense cells in the introduced blood sample; and derive blood-sample measurements of cells in the introduced blood sample, and further perform the analyzing operation in the blood measuring mode to: analyze the blood-sample measurements; and count a particular type of cells in the introduced blood sample based on the analyzed blood-sample measurements; and
perform the sensing operation in the body fluid measuring mode to: introduce the body fluid sample into said multi-mode detector; operate said multi-mode detector to sense cells in the introduced body fluid sample; and derive body-fluid-sample measurements of cells in the introduced body fluid sample, and further perform the analyzing operation in the body fluid measuring mode to: analyze the body-fluid-sample measurements; and count the particular type of cells in the introduced body fluid sample based on the analyzed body-fluid-sample measurements.

13. The sample analyzer according to claim 12, wherein the particular type of cells are blood cells.

14. The sample analyzer according to claim 12, wherein the particular type of cells are white blood cells or a subclass of the white blood cells.

15. The sample analyzer according to claim 12, wherein the particular type of cells are red blood cells.

16. The sample analyzer according to claim 12, wherein the particular type of cells are platelets.

17. The sample analyzer according to claim 12, wherein the sensing operation performed in the blood measuring mode comprises sensing the particular type of cells in the introduced blood sample for a first measurement time, and
the sensing operation performed in the body fluid measuring mode comprises sensing the particular type of cells in the introduced body fluid sample for a second measurement time, wherein the second measurement time is longer than the first measurement time according to a cell concentration of the sample.

18. The sample analyzer according to claim 12, wherein the sensing operation performed in the body fluid measuring mode comprises automatically initiating pre-washing said multi-mode detector to reduce a carryover effect on measurements of the body fluid sample, wherein the controller is programmed to automatically initiate said pre-washing before introducing the body fluid sample into said multi-mode detector during said sensing operation in the body fluid measuring mode, and wherein said automatically initiated pre-washing includes more than one washing of said multi-mode detector.

19. A sample analyzer comprising:
a plurality of detectors each configured to sense cells in a sample, the sample selectively comprising (i) a blood sample or (ii) a body fluid sample, wherein the body fluid sample contains body fluid, other than blood, which is selected from a group consisting of cerebrospinal fluid, thoracic fluid, abdominal fluid, fluid collected in a cardiac sac, synovial fluid, dialysate from peritoneal dialysis, and intraperitoneal rinse;
a controller programmed to selectively operate the sample analyzer in a blood measuring mode or a body fluid measuring mode, wherein the blood measuring mode includes a sequence of operations for measuring cells in the blood sample, and the body fluid measuring mode includes a sequence of operations for measuring cells in the body fluid sample, and wherein the plurality of detectors includes one or more multi-mode detectors configured to operate in both the blood measuring mode and the body fluid measuring mode, the controller programmed to:
perform the sequence of operations in the blood measuring mode to: introduce the blood sample into a multi-mode detector; operate said multi-mode detector to sense cells in the introduced blood sample; and derive blood-sample measurements of cells in the introduced blood sample; and
perform the sequence of operations in the body fluid measuring mode to: introduce the body fluid sample into said multi-mode detector; operate said multi-mode detector to sense cells in the introduced body fluid sample; and derive body-fluid-sample measurements of cells in the introduced body fluid sample, wherein the sequence of operations performed in the body fluid measuring mode comprises automatically initiating pre-washing said multi-mode detector to reduce a carryover effect on the body-fluid-sample measurements, wherein the controller is programmed to automatically initiate said pre-washing before introducing the body fluid sample into said multi-mode detector during said sequence of operations in the body fluid measuring mode.

20. A sample analyzer comprising:
a plurality of detectors each configured to sense cells in a sample, the sample selectively comprising (i) a blood sample or (ii) a body fluid sample, wherein the body fluid sample contains body fluid, other than blood, which is selected from a group consisting of cerebrospinal fluid, thoracic fluid, abdominal fluid, fluid collected in a cardiac sac, synovial fluid, dialysate from peritoneal dialysis, and intraperitoneal rinse;
a controller programmed to selectively operate the sample analyzer in a blood measuring mode or a body fluid measuring mode, wherein the blood measuring mode includes a sequence of operations for measuring cells in the blood sample, and the body fluid measuring mode includes a sequence of operations for measuring cells in the body fluid sample, the controller programmed to:
perform the sequence of operations in the blood measuring mode to: analyze blood-sample measurements of cells in the blood sample; count each of five types of white blood cells in the blood sample; and separately display in a screen a count of each of said five types of white blood cells; and
perform the sequence of operations in the body fluid measuring mode to: analyze body-fluid-sample measurements of cells in the body fluid sample; count mono-nucleated cells and poly-nucleated cells in the body fluid sample; and separately display in a screen a count of the mono-nucleated cells and a count of the poly-nucleated cells.

21. A sample analyzer comprising:
a plurality of detectors each configured to optically or electrically sense cells in a sample, the sample selectively comprising (i) a blood sample or (ii) a body fluid sample, wherein the body fluid sample contains body fluid, other than blood, which is selected from a group consisting of cerebrospinal fluid, thoracic fluid, abdominal fluid, fluid collected in a cardiac sac, synovial fluid, dialysate from peritoneal dialysis, and intraperitoneal rinse;
a controller programmed to selectively operate the sample analyzer in a blood measuring mode or a body fluid measuring mode, wherein the blood measuring mode includes a sequence of operations for measuring cells in the blood sample, and the body fluid measuring mode includes a sequence of operations for measuring cells in the body fluid sample, the controller programmed to:
(A) perform the sequence of operations in the body fluid measuring mode to: sense cells in a first body fluid sample; analyze first measurements of the cells sensed in the first body fluid sample; and count red blood cells in the first body fluid sample, and
(B) perform the sequence of operations in the body fluid measuring mode to: sense cells in a second body fluid sample; analyze second measurements of the cells sensed in the second body fluid sample; count mono-nucleated cells and poly-nucleated cells in the second body fluid sample; and separately display in a screen a count of the red blood cells, a count of the mono-nucleated cells and a count of the poly-nucleated cells.

22. The sample analyzer according to claim 1, wherein the controller is programmed to remain in the body fluid measuring mode after completing the sequence of operations in the body fluid measuring mode until the body fluid measuring mode is manually switched to the blood measuring mode.

23. The sample analyzer according to claim 12, wherein the controller is programmed to remain in the body fluid measuring mode after completing the sequence of operations in the body fluid measuring mode for measuring cells in one body fluid sample until the body fluid measuring mode is manually switched to the blood measuring mode.

24. The sample analyzer according to claim 19, wherein the controller is programmed to remain in the body fluid measuring mode after completing the sequence of operations in the body fluid measuring mode for measuring cells in one body fluid sample until the body fluid measuring mode is manually switched to the blood measuring mode.

25. The sample analyzer according to claim 20, wherein the controller is programmed to remain in the body fluid measuring mode after completing the sequence of operations in the body fluid measuring mode for measuring cells in one body fluid sample until the body fluid measuring mode is manually switched to the blood measuring mode.

26. The sample analyzer according to claim 21, wherein the controller is programmed to remain in the body fluid measuring mode after completing the sequence of operations in the body fluid measuring mode for measuring cells in one body fluid sample until the body fluid measuring mode is manually switched to the blood measuring mode.

27. The sample analyzer according to claim 3, wherein said automatically initiated pre-washing includes more than one washing of said multi-mode detector.

28. The sample analyzer according to claim 19, wherein said automatically initiated pre-washing includes more than one washing of said multi-mode detector.

* * * * *

UNITED STATES PATENT AND TRADEMARK OFFICE
CERTIFICATE OF CORRECTION

PATENT NO. : 10,401,350 B2
APPLICATION NO. : 16/214417
DATED : September 3, 2019
INVENTOR(S) : Takaaki Nagai et al.

Page 1 of 1

It is certified that error appears in the above-identified patent and that said Letters Patent is hereby corrected as shown below:

In the Claims

In Column 17, Claim 8, Line 54, delete "sensing" and replace with -- analyzing --.

In Column 17, Claim 9, Line 61, delete "operations" and replace with -- operation --.

Signed and Sealed this
Twenty-first Day of April, 2020

Andrei Iancu
*Director of the United States Patent and Trademark Office*